US007615537B2

(12) United States Patent
Scaria et al.

(10) Patent No.: US 7,615,537 B2
(45) Date of Patent: Nov. 10, 2009

(54) METHODS FOR TREATING BLOOD COAGULATION DISORDERS

(75) Inventors: Abraham Scaria, Framingham, MA (US); Samuel C. Wadsworth, Shrewsbury, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 10/057,620

(22) Filed: Oct. 25, 2001

(65) Prior Publication Data

US 2003/0229036 A1 Dec. 11, 2003

Related U.S. Application Data

(60) Provisional application No. 60/307,492, filed on Jul. 24, 2001, provisional application No. 60/243,046, filed on Oct. 25, 2000.

(51) Int. Cl.
*A61K 48/00* (2006.01)
*C12N 15/63* (2006.01)

(52) U.S. Cl. ..................................... 514/44; 435/320.1

(58) Field of Classification Search ................... 514/44, 514/2; 424/93.2, 450, 468, 486; 435/230.1, 435/91.1, 320.1
See application file for complete search history.

(56) References Cited

U.S. PATENT DOCUMENTS

| | | | | |
|---|---|---|---|---|
| 4,784,950 | A | 11/1988 | Hagen et al. | |
| 5,739,101 | A * | 4/1998 | Roy et al. | 514/2 |
| 5,824,639 | A * | 10/1998 | Berkner | 514/12 |
| 6,210,929 | B1 | 4/2001 | Schlokat et al. | |
| 2003/0192066 | A1 * | 10/2003 | Zhang et al. | 800/8 |

FOREIGN PATENT DOCUMENTS

| | | | |
|---|---|---|---|
| EP | 0775750 A2 | | 5/1997 |
| WO | WO 97/20043 | | 6/1997 |
| WO | WO 00/23116 | | 4/2000 |
| WO | WO 01/70763 | * | 9/2001 |

OTHER PUBLICATIONS

U.S. Appl. No. 60/191,331, filed Sep. 2001, Hish et al.*
Margaritis et al., Blood, vol. 98, No. 11, Par 1, pp. 696a, abstract # 2908, Nov. 16, 2001.*
Manno, Semin Hematol 40 (suppl 3):23-28, 2003.*
Greengard et al., Thrombosis and Haemostasis, vol. 82, 2:555-561, 1999.*
VandenDriessche et al., Current Gene Therapy, 1:301-315, 2001.*
Seidah et al. (1999) Brain Research, vol. 848, 45-62.*
Miller, G. et al., "Expression of factor VII by muscle cells in vitro and in vivo following direct gene transfer: modelling gene therapy for haemophilia", Gene Therapy, vol. 2, No. 10: pp. 736-742, Dec. 1, 1995.
Shah, A.M. et al.. "Manipulation of the membrane binding site of vitamin K-dependent proteins: Enchanced biolgoical function of human factor VII", Proceedings of the National Academy of Sciences, USA, vol. 95, No. 8: pp. 4229-4234, Apr. 14, 1998.
Arkin S. et al., "Activated recombinant human coagulation factor VII therapy for intracranial hemorrhage in patients with hemophilia A or B with inhibitors: Results of the NovoSeven emergency-use program", Database Biosis Online, Biosciences Information Service, Database Accession No. PREV1999900229958 XP002228408 abstract & Haemostasis, vol. 28, No. 2: pp. 93-98, Mar. 1998.
Roman, Drews et al., "Proteolytic maturation of protein C upon engineering the mouse mammary gland to express furin", Database Biosis Online, Biosciences Information Service, Database Accession No. PREV199698601105 XP 002228409 abstract & Proceedings of the National Academy of Sciences of the United States, vol. 92, No. 23: pp. 10462-10466, 1995.
Hart, C E et al., "Characterization of a cDNA coding for human factor VII", Database Medline Online, Database Accession No. NLM3486420 XP002228410 abstract & Proc Natl Acad Sci, USA. vol. 83, pp. 2412-2416, 1986.
Paris, Margaritis et al., "Long-term expression of activated FVII in vivo following AAV-mediated liver gene transfer: Implications for treatment with continuous infusion of recombinant activated FVII", Database Biosis Online, Biosciences Information Service, Database Accession No. PREV200200220527 XP 002228411 abstract Blood, vol. 98, No. 11, Part 1, pp. 696a, Nov. 16, 2001.

* cited by examiner

*Primary Examiner*—Anne Marie S Wehbe

(57) ABSTRACT

The present invention relates to a method of treating an individual having a blood coagulation defect (e.g., hemophilia A, hemophilia B), comprising administering to the individual an effective amount of a DNA vector encoding modified Factor VII (FVII), wherein the modified Factor VII leads to generation of Factor VIIa in vivo. In a particular embodiment, the invention pertains to a method of treating an individual having a blood coagulation defect comprising administering to the individual an effective amount of a nucleic acid encoding a modified FVII wherein the modified FVII comprises a signal which codes for precursor cleavage by furin at the activation cleavage site of the modified FVII. The invention also relates to a method of treating an individual having a blood coagulation disorder comprising administering to the individual an effective amount of a nucleic acid encoding the light chain of human FVII and a nucleic acid encoding the heavy chain of human FVII operably linked to a leader sequence. Compositions, expression vectors and host cells comprising nucleic acid which encodes a modified Factor VII, wherein the modified Factor VII leads to generation of Factor VIIa in vivo is also encompassed by the present invention.

49 Claims, 9 Drawing Sheets

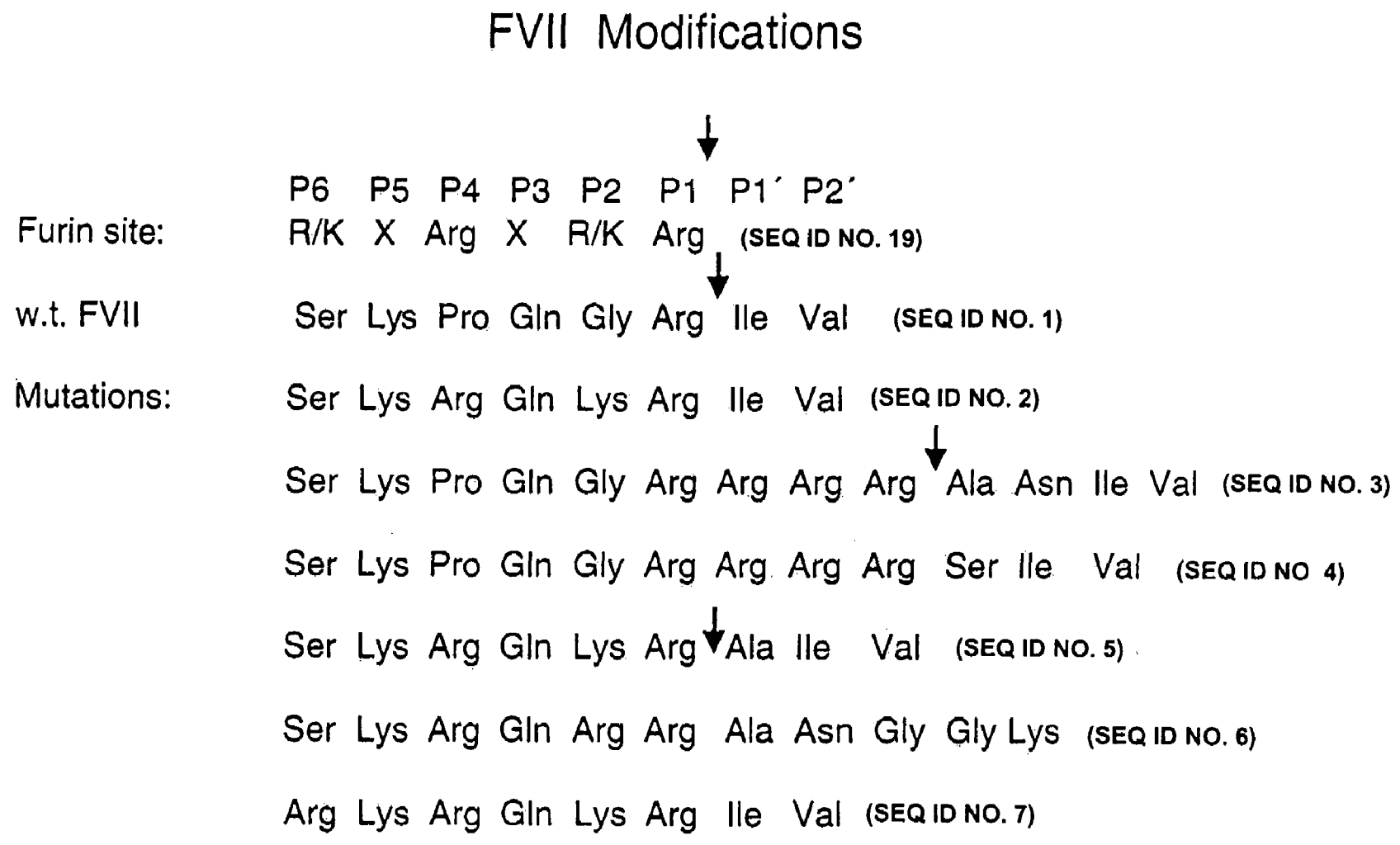

FVII Modifications

| | P6 | P5 | P4 | P3 | P2 | P1 | P1´ | P2´ | | | | | |
|---|---|---|---|---|---|---|---|---|---|---|---|---|---|
| Furin site: | R/K | X | Arg | X | R/K | Arg | (SEQ ID NO. 19) | | | | | | |
| w.t. FVII | Ser | Lys | Pro | Gln | Gly | Arg | Ile | Val | (SEQ ID NO. 1) | | | | |
| Mutations: | Ser | Lys | Arg | Gln | Lys | Arg | Ile | Val | (SEQ ID NO. 2) | | | | |
| | Ser | Lys | Pro | Gln | Gly | Arg | Arg | Arg | Arg | Ala | Asn | Ile | Val (SEQ ID NO. 3) |
| | Ser | Lys | Pro | Gln | Gly | Arg | Arg | Arg | Arg | Ser | Ile | Val | (SEQ ID NO 4) |
| | Ser | Lys | Arg | Gln | Lys | Arg | Ala | Ile | Val | (SEQ ID NO. 5) | | | |
| | Ser | Lys | Arg | Gln | Arg | Arg | Ala | Asn | Gly | Gly | Lys | (SEQ ID NO. 6) | |
| | Arg | Lys | Arg | Gln | Lys | Arg | Ile | Val | (SEQ ID NO. 7) | | | | |

FIG. 2

FVII Modifications

|  | P6 | P5 | P4 | P3 | P2 | P1 | P1' | P2' |  |
|---|---|---|---|---|---|---|---|---|---|
| SKI-1 site: | R/K | X | R/K | X | L/V/F | Z ↓ | | | (SEQ ID NO. 20) |
| w.t. FVII | Ser | Lys | Pro | Gln | Gly | Arg ↓ | Ile | Val | (SEQ ID NO. 1) |
| Mutations: | R/K | Lys | R/K | Gln | L/V/F | Arg | Ile | Val | (SEQ ID NO. 9) |

FIG. 3

1:100 diluted thromboplastin times

Modified aPTT assay

METHODS FOR TREATING BLOOD COAGULATION DISORDERS

This application claims the benefit of priority under 35 U.S.C. § 119(e) to U.S. Provisional Application Ser. Nos. 60/243,046 filed Oct. 25, 2000 and 60/307,492 filed Jul. 24, 2001 respectively. The contents of these applications are hereby incorporated by reference into the present disclosure.

BACKGROUND OF THE INVENTION

Hemophilia is an X-linked bleeding disorder that results from a deficiency in coagulation factor VIII (hemophilia A) or factor IX (hemophilia B). Patients are conventionally treated by protein replacement therapies using plasma-derived or recombinant factor VIII or factor IX. Gene therapies for both hemophilia A and B are in various stages of pre-clinical and clinical trails. However, 25% of hemophilia A patients develop inhibitors (e.g., antibodies) to factor VIII and about 5% of hemophilia B patients generate inhibitors to factor IX. These inhibitors lead to the ineffectiveness of protein replacement or gene replacement therapies.

It is known that basal levels of Factor VIIa in plasma are greatly reduced in patients with hemophilia B (Factor IX deficiency) and, to a lesser extent, patients with hemophilia A (Factor VIII deficiency). Wildgoose et al., *Blood* 1:25-28 (1992). In the absence of activated FVIIa, the intrinsic blood clotting pathway involving FVII and FIX, is severely limited in effective coagulation. Recently, recombinant activated Factor VII (rFVIIa, NovoSeven, Novo, Nordisk) has been shown to have therapeutic value to bypass or correct the coagulation defects in hemophilia A and B patients with inhibitors, especially in patients with inhibitors who were undergoing surgical procedures. However, recombinant FVIIa is expensive to manufacture. Anther critical problem is the short half life (2 hours) of recombinant FVIIa. Therefore, recombinant FVIIa therapy requires an intravenous infusion of high doses of the protein every 2 hours.

A need exists for alternative therapies for blood coagulation disorders such as hemophilia.

SUMMARY OF THE INVENTION

In the methods of the present invention, activated Factor VII is provided to a patient suffering from a coagulation defect, such as hemophilia. The Factor VII is delivered via DNA vectors, which may be viral or non-viral in origin. In one preferred embodiment, the activated Factor VII is provided using a DNA vector encoding a modified FVII. This modified FVII comprises a cleavage site, such as a furin cleavage site or other appropriate cleavage site, such that the modified Factor VII molecule is cleaved to form the light chain and heavy chain of Factor VII, which can then form suitable disulfide bonds to form activated Factor VII. In other preferred embodiments, activated Factor VII is supplied using DNA vectors which separately encode the light chain of Factor VII and the heavy chain of Factor VII, such that no cleavage is necessary, and the individual chains are both present and can form suitable disulfide bonds to form activated Factor VII. The individual DNA vectors which separately encode the light chain of Factor VII and the heavy chain of Factor VII may be provided on the same plasmid, either as two separate expression cassettes with separate regulatory sequences, or as part of a single polycistronic expression cassette. Alternatively, the individual DNA vectors which separately encode the light chain of Factor VII and the heavy chain of Factor VII may be provided on separate plasmids or vehicles which may be co-transformed into a single cell, so that both individual chains are present and can form suitable disulfide bonds to form activated Factor VII. In certain embodiments of the present invention, surrounding conditions, such as pH, temperature and electrovalent charges in the medium can be adjusted to optimally promote proper disulfide bonding.

The present invention further relates to method of treating an individual having blood coagulation defect (e.g., hemophilia A, hemophilia B), comprising administering to the individual an effective amount of a DNA vector expressing modified Factor VII (FVII), wherein the modified Factor VII leads to generation of Factor VIIa in vivo. In one embodiment, the modified Factor VII comprises an amino acid sequence which codes for a signal for precursor cleavage by the protease furin at the activation cleavage site of the modified Factor VII. For example, the amino acid signal in the modified FVII can comprise an Arg149-X150-Lys151-Arg152 (SEQ ID NO. 17) signal sequence or an Arg149-X150-Arg151-Arg152 (SEQ ID NO. 18)signal sequence, such as an Arg149-Gln150-Lys151-Arg152 (SEQ ID NO. 10). In another embodiment, the DNA vector encoding modified Factor VII is administered as a combination of two compositions wherein the first composition comprises the light chain (from about amino acid 1 to about amino acid 152) of human Factor VII and the second composition comprises the heavy chain from about (amino acid 153 to about amino acid 406) of human Factor VII and (operably linked to) a leader sequence (e.g., derived from a cytokine or a clotting factor). The DNA encoding modified Factor VII of the present invention can be administered as any gene transfer vector, such as viral vectors, including adenovirus, AAV, retrovirus and lentivirus, as well as plasmid DNA with or without a suitable lipid or polymer carriers, and is administered under conditions in which the nucleic acid is expressed in vivo. Alternatively, the DNA encoding modified FVII can be administered as naked DNA or in association with an amphiphilic compound, such as lipids or compounds, or with another suitable carrier.

The present invention also relates to methods of treating hemophilia in an individual, comprising administering to the individual an effective amount of a DNA vector encoding modified Factor VII wherein the modified Factor VII leads to generation of Factor VIIa in vivo. In one embodiment, the present invention relates to a method of treating hemophilia in an individual who has developed an inhibitor of Factor VII, comprising administering to the individual an effective amount of a DNA vector encoding modified Factor VII wherein the modified Factor VII leads to generation of Factor VIIa in vivo. In another embodiment, the invention relates to a method of treating hemophilia in an individual who has developed an inhibitor of Factor IX, comprising administering to the individual an effective amount of a DNA vector encoding modified Factor VII wherein the modified Factor VII leads to generation of Factor VIIa in vivo.

In a particular embodiment, the invention pertains to a method of treating an individual having a blood coagulation defect comprising administering to the individual an effective amount of a DNA vector comprising a nucleic acid encoding a modified FVII wherein the modified FVII comprises a signal which codes for precursor cleavage by furin at the activation cleavage site of the modified FVII.

The invention also relates to a method of treating an individual having a blood coagulation disorder comprising administering to the individual an effective amount of a DNA vector comprising a nucleic acid encoding the light chain of human FVII and a nucleic acid encoding the heavy chain of human FVII operably linked to a leader sequence.

Compositions comprising DNA vectors encoding a modified Factor VII, wherein the modified Factor VII leads to generation of Factor VIIa in vivo is also encompassed by the present invention. In one embodiment, the modified Factor VII comprises an amino acid sequence which codes for a signal for precursor cleavage by furin at the activation cleavage site of the modified Factor VII.

The present invention also relates to an expression vector comprising nucleic acid encoding a modified Factor VII, wherein the modified Factor VII leads to generation of Factor VIIa in vivo. In one embodiment, the nucleic acid sequence encodes an amino acid sequence which includes a signal for precursor cleavage by furin at the activation cleavage site of the modified Factor VII. In another embodiment, the nucleic acid construct comprises two expression constructs which encode a modified Factor VII wherein the first expression construct comprises amino acids 1-152 of human Factor VII and the second expression comprises amino acids 153-406 of human Factor VII and a leader sequence.

The present invention also relates to host cells comprising a DNA vector comprising a nucleic acid which encodes a modified Factor VII, wherein the modified Factor VII leads to generation of Factor VIIa in vivo. In one embodiment, the nucleic acid sequence encodes an amino acid sequence which includes a signal for precursor cleavage by furin at the activation cleavage site of the modified Factor VII. In another embodiment, the nucleic acid construct comprises two expression constructs which encode a modified Factor VII wherein the first expression construct comprises amino acids 1-152 of human Factor VII and the second expression comprises amino acids 153-406 of human Factor VII and a leader sequence.

Host cells comprising a DNA vector encoding a modified Factor VII in accordance with the present invention may be cultured ex vivo and administered to or implanted into an individual suffering from a blood coagulation defect or disease such as hemophilia A, hemophilia B or Factor VII deficiency.

Thus, the present invention provides for an alternative treatment of blood clotting defects, such as hemophilia A or hemophilia B, in an individual, particularly where the individual has developed inhibitors to conventional treatment (e.g., inhibitors against FVIII and/or FIX).

BRIEF DESCRIPTION OF THE FIGURES

FIG. 2 illustrates examples of mutations to the FVII amino acid sequence which can be engineered at the nucleotide level in order to create a furin cleavage site at the activation site of FVII.

FIG. 3 illustrates examples of mutations to the FVII amino acid sequence which can be engineered at the nucleotide level in order to create an SK1 cleavage site at the activation site of FVII.

DETAILED DESCRIPTION OF THE INVENTION

Figure 1:
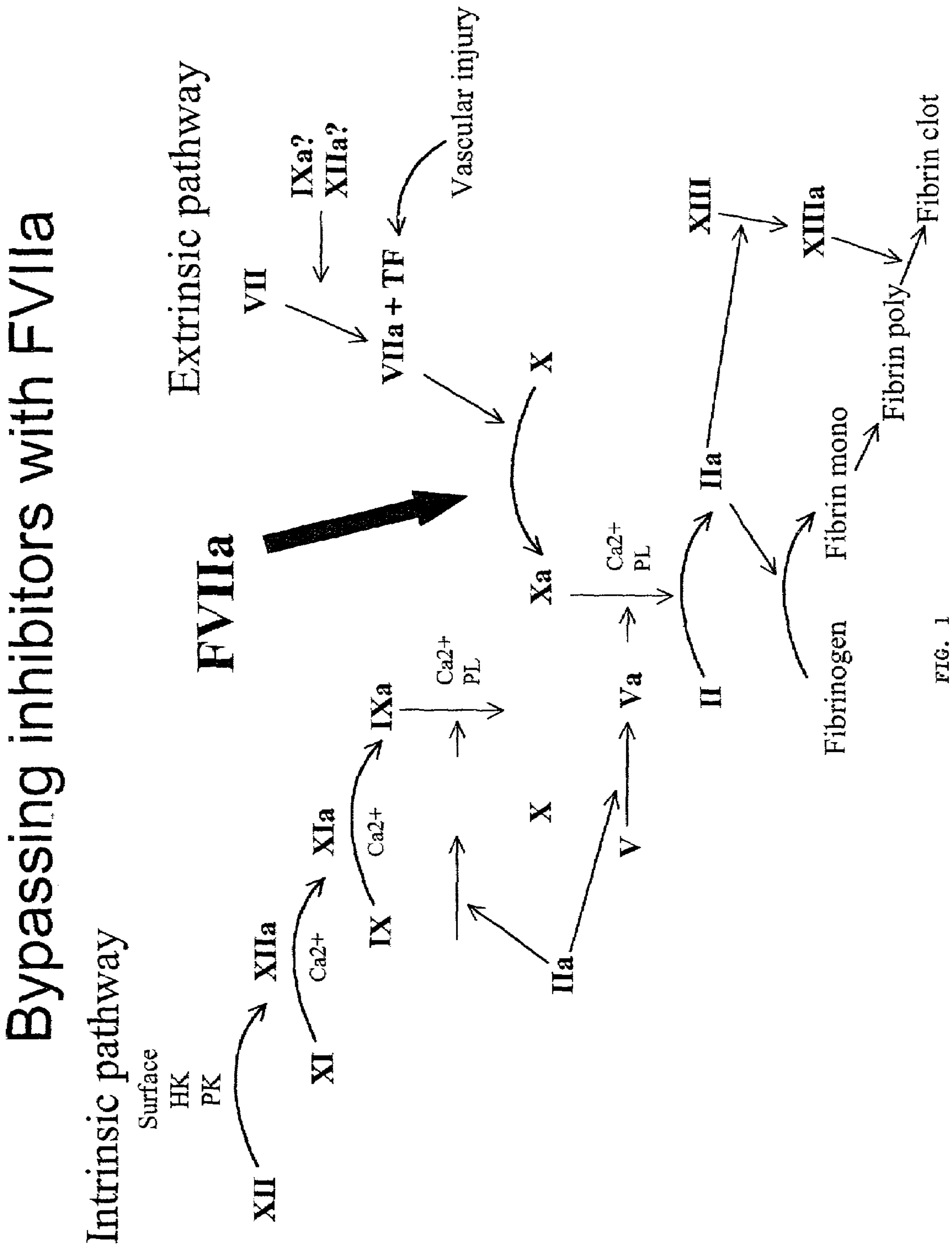
FIG. 1 illustrates the intrinsic and extrinsic pathways for fibrin clot formation and the mechanism by which FVIIa can act.
Figure 4A:
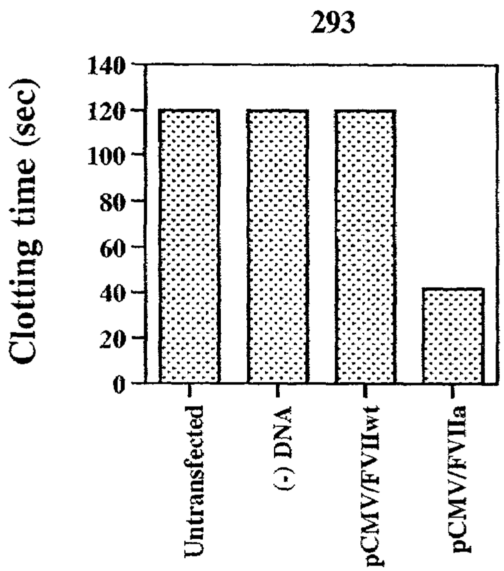
FIGS. 4A and 4B illustrates clotting time of 293 cells [FIG. 4A] and Hep3B cells [FIG. 4B] untransfected, and transfected with FVII and FVIIa.
Figure 4B:
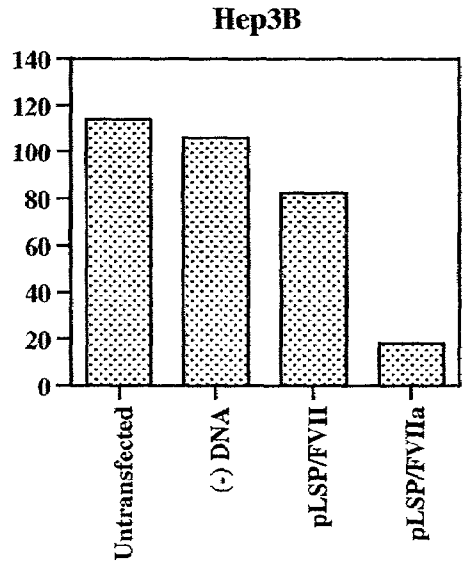

Factor VII is a single chain glycoprotein (mol. wt. 50,000) of 406 amino acids that is secreted into the blood where it circulates in a zymogen form. In vitro, FVII can be proteolytically activated to activated Factor FVII, or FVIIa, by the action of activated coagulation factors Factor X (FXa), Factor IX (FIXa), Factor XII (FXIIa) or Factor II (FIIa). FVIIa does not promote coagulation by itself, but can complex with tissue factor (TF) exposed at the site of injury. The FVIIa/TF complex can convert FX to FXa, thereby inducing local hemostasis at the site of injury. Activation of FVII to FVIIa involves proteolytic cleavage at a single peptide bond between Arg-152 and Ile-153, resulting in a two-chain molecule consisting of a light chain of 152 amino acid residues and a heavy chain of 254 amino acid residues held together by a single disulfide bond. Hemophilia patients have normal levels of FVII, however, they suffer from a relative deficiency in FVIIa and other activated clotting factors.

The present invention further relates to DNA expression vectors and constructs, which may be useful for gene therapy by providing an effective amount of activated Factor VII to the plasma, or to a suitable depot organ, such as liver or lung, within a patient. The DNA vectors may comprise nucleic acid encoding a modified Factor VII, wherein the modified Factor VII leads to generation of Factor VIIa in vivo. Various embodiments of the invention are possible, each of which is capable of producing an effective amount of activated FVII in a patient who is otherwise lacking sufficient clotting factors to achieve blood coagulation. The present invention in various embodiments thus comprises (1) administering DNA vectors which encode activated FVII; (2) administering DNA vectors which encode a modified FVII such that FVII will be cleaved to form activated FVII; (3) administering DNA vectors which encode FVII, together with administration of an activator [e.g., FIXa, FXa or FXIIa] such that FVII will be cleaved to form activated FVIIa; (4) administering DNA vectors which separately encode the light chain of FVII and the heavy chain of FVII, such that both chains are present in a cell and can associate, form disulfide bonds to form activated FVII.

Suitable DNA vectors for modified Factor VII may have been modified to create an activation cleavage site, such as a furin or other subtilisin cleavage site, at an appropriate position within the Factor VII DNA sequence. For example, a modification may be made in the area of about amino acid 147 through about 154 of human Factor VII to create an appropriate cleavage site. The DNA vector may be a viral vector such as an adenovirus vector, a partially-deleted adenovirus vector, a fully-deleted adenovirus vector, an adeno-associated virus vector, a pseudoadenovirus, a retrovirus vector and a lentivirus vector. An example of an alternate cleavage enzyme which may be suitable for use in the present invention is SK1. Seidah et al. (1999) PNAS, Vol. 96, 1321-1326.

Alternative DNA expression vectors and constructs for use in the present invention include more than one DNA vector which separately encode the light chain of Factor VII, which begins at about amino acid 1 and continues until about amino acid 147 to about amino acid 152 of human Factor VII; and the heavy chain of Factor VII, which begins from about amino acid 147 to amino acid 154 and continues to about amino acid 406 human Factor VII. The DNA vector encoding the heavy chain of Factor VII may preferably be designed to include a separate leader sequence, such as a leader sequence of a protein selected from the group consisting of: a cytokine, growth factor, colony stimulating factor and a clotting factor. In addition, the present invention comprises nucleic acid constructs comprising polycistronic expression cassettes, wherein the expression cassette comprises (a) nucleic acids encoding the light chain of Factor VII and (b) nucleic acids encoding the heavy chain of Factor VII, and wherein (a) and (b) are separated by an internal ribosome entry site or other suitable spacer for expression of polycistronic messages.

The present invention further includes methods of treating hemophilia and methods of promoting blood coagulation by administering a DNA vector which encodes human Factor VII. Such methods may use viral or non-viral vectors, such as adenovirus, adeno-associated viruses, retroviruses, lentiviruses, and recombinant versions of the above, as well as naked plasmid DNA, and DNA in conjunction with a suitable compound, such as a cationic lipid or amphiphilic polymers. In preferred embodiments, the method may further include co-administering of an activating amount of an activator protein, such as FIXa, Fxa or FXIIa. The activator may be administered in the form of a suitable protein formulation, or may be administered using a DNA vector which encodes the activator. The activator may be administered immediately prior to, simultaneously with, or subsequently to administration of the DNA vector which encodes Factor VII.

In one embodiment, the present invention provides DNA vectors encoding a modified version of clotting Factor VII such that it leads to generation of (or can be converted to) activated Factor VII (FVIIa) in vivo. Accordingly, the present invention provides a method of treating an individual having a blood coagulation defect comprising administering to the individual an effective amount of a DNA vector encoding the modified FVII described herein, wherein the modified FVII leads to generation of (is converted to) FVIIa in vivo.

The DNA vectors useful in the present invention include both viral and non-viral vectors. The viral DNA vectors useful in the present invention may include adenoviral, AAV, retroviral and lentiviral vectors. The non-viral DNA vectors may include amphiphilic compounds, polymers and lipids, as well as 'naked DNA' vectors.

Blood coagulation defects associated with defects in one or more of the clotting factors can be treated using the methods described herein. Examples of blood clotting defects which can be treated using the methods described herein include hemophilia (e.g., hemophilia A, hemophilia B) and blood clotting defects associated with the presence of inhibitors (e.g., antibodies) of a (one or more) clotting factor (e.g., FVII, FVIII, FIX) in an individual. The modified FVII of the present invention is suitable to administer to a variety of individuals, such as mammals, and particularly, humans.

In one embodiment, a signal (sequence) for precursor cleavage by a protease is introduced into the activation cleavage site of FVII, wherein FVIIa is produced upon cleavage of the signal by the protease. Preferably, the signal is cleaved by a protease that is present in cells into which the modified FVII is introduced. Any suitable signal for precursor cleavage by a protease which, when cleaved results in generation of FVIIa, can be introduced into the activation cleavage site of the modified FVII of the present invention. For example, a signal which is cleaved by furin [also known as PACE, see U.S. Pat. No. 5,460,950], other subtilisins [including PC2, PC1/PC3, PACE4, PC4, PC5/PC6 and LPC/PC7/PC8/SPC7; Nakayama, *Biochem. J.,* 327:625-635 (1997)] enterokinase [see U.S. Pat. No. 5,270,181 or chymotrypsin may be of use, and can be introduced into the cleavage activation site of FVII for use in the present invention. The disclosure of each of the above documents is hereby incorporated herein by reference.

In a particular embodiment, the modified FVII comprises an amino acid sequence which codes for a signal for precursor cleavage by furin. Furin is a ubiquitously expressed protease that resides in the trans-golgi and processes protein precursors before their secretion. Furin cleaves at the COOH-terminus of its consensus recognition sequence, Arg-X-Lys-Arg (SEQ ID NO. 17) or Arg-X-Arg-Arg, (SEQ ID NO. 18) and to a lesser extent, Arg-X-X-Arg (SEQ ID NO. 8). The amino acid (aa) sequence at position 149-152 of human FVII is Pro-Gln-Gly-Arg (SEQ ID NO. 11). An example of this embodiment is one in which the nucleotide sequence of FVII is modified such that Pro-149 is changed to Arg-149 and Gly-151 is changed to Lys-151. The resulting amino acid sequence Arg-Gln-Lys-Arg (SEQ ID NO. 10) is a signal for precursor cleavage by the protease furin. Other examples for producing a furin cleavage site in the nucleotide sequence of FVII include substituting amino acids 147 through 150, 148 through 151, 150 through 153 or amino acids 151 through 154 with suitable amino acids to produce a furin cleavage site with the sequence Arg-X-Lys-Arg (SEQ ID NO. 17) or Arg-X-Arg-Arg(SEQ ID NO 18).

In another preferred embodiment, the DNA vector encoding the modified FVII containing a furin cleavage site may be co-expressed with a DNA vector encoding furin. In this manner, FVIIa could be produced in cells that would not ordinarily express furin, and thus which would not ordinarily cleave the modified FVII product to form FVIIa.

In the modified FVII coding DNA vectors described herein, in place of furin, other proteases, such as those of the subtilisin family, can be used. These include PC2, PC1/PC3, PACE4, PC4, PC5/PC6 and LPC/PC7/PC8/SPC7. See Nakayama, *Biochem. J.,* 327:625-635 (1997) and the references cited therein for their disclosure of the amino acid sequences and coding DNA sequences for these subtilisin convertase proteins. The disclosure of these publications is hereby incorporated herein by reference.

In other embodiments of the present invention, the DNA vectors encoding the heavy chain and light chain of FVII can be separated and introduced into the same cell(s). In one particular embodiment, nucleic acid (e.g., cDNA) encoding human FVII is split into two expression cassettes. The first cassette encodes the light chain (from about amino acid 1 to about amino acid 152) of human FVII which includes the pre-pro leader sequence of human FVII. The second cassette encodes the heavy chain of human FVII (from amino acid 153 to about amino acid 406) with a pre-pro leader sequence from any well secreted protein fused to the N-terminus. For example, the pre-pro leader sequence can be derived from a cytokine (e.g., interleukins, including IL-1, IL-2, IL-3, IL-4, IL-6, IL-8, IL-9, IL-11, IL-12, IL-13, IL-14, IL-15 and IL-16), colony stimulating factors such as G-CSF, GM-CSF and M-CSF, growth factors, such as IGF, KGF, BGF, FGF, hormones and clotting factors (e.g., Factors I through Factors XIII, including FV, FVII, FVIII, FIX and FX). The two expression cassettes may be cloned into the same or different regions of a vector, such as adenovirus (e.g., E1 and/or E3 regions), partially-deleted adenovirus or fully-deleted adenovirus. In another embodiment of the present invention, the heavy and light chains may be introduced into the same cell using two different vectors, such as through co-transformation. In yet another embodiment of the present invention, the light chain and heavy chain can be introduced into a cell on a single, polycistronic expression cassette. The coding sequences of the light and heavy chain in such a polycistronic cassette are preferably driven by a single promoter and are preferably separated by an internal ribosome entry site ["IRES"]. By means of the above embodiments, the light chain and heavy chain of FVIIa are thus expressed in the same cell in vivo upon introduction of this vector via intravenous, intramuscular, intraportal or other route of administration.

Additional, modified versions of clotting Factor VII which generate (or are converted to) activated Factor VII (FVIIa) in vivo similar to those described herein, can be prepared by those of skill in the art. Such modified versions of FVII can be assessed for their ability to convert to FVIIa in vivo using a variety of known assays for FVIIa activity.

The DNA molecules encoding FVII for use in the present invention can be derived from any suitable mammalian source and modified as described herein. For example, the FVII can be of human origin (U.S. Pat. No. 4,784,950) or of bovine origin (Takeya, et al., *J. Biol. Chem.,* 263:14868-14872 (1988)), as well as other species' origin, and may be chimeric, for example including domains of human and non-human FVII [see, for example, by analogy U.S. Pat. Nos. 5,364,771 and 5,563,045 (FVIII)]. The modifications described herein can be introduced into other mammalian FVII as they are identified, and the ability of the resulting modified FVII to produce FVIIa in vivo, can be assessed using known methods. In addition, the DNA encoding modified FVII described herein can be obtained from commercial sources, recombinantly produced or chemically synthesized. Sequence modifications of the modified FVII described herein can be accomplished using a variety of techniques. For example site-directed mutagenesis and/or enzymatic cleavage can be used.

In the methods of the present invention, activated Factor VII is provided to a patient suffering from a coagulation defect, such as hemophilia. The Factor VII is delivered via DNA vectors, which may be viral or non-viral in origin. In one preferred embodiment, the activated Factor VII is provided using a DNA vector encoding a modified FVII. This modified FVII comprises a cleavage site, such as a furin cleavage site or other appropriate cleavage site, such that the modified Factor VII molecule is cleaved to form the light chain and heavy chain of Factor VII, which can then form suitable disulfide bonds to form activated Factor VII. In other preferred embodiments, activated Factor VII is supplied using DNA vectors which separately encode the light chain of Factor VII and the heavy chain of Factor VII, such that no cleavage is necessary, and the individual chains are both present and can form suitable disulfide bonds to form activated Factor VII. The individual DNA vectors which separately encode the light chain of Factor VII and the heavy chain of Factor VII may be provided on the same plasmid, either as two separate expression cassettes with separate regulatory sequences, or as part of a single polycistronic expression cassette. Alternatively, the individual DNA vectors which separately encode the light chain of Factor VII and the heavy chain of Factor VII may be provided on separate plasmids or vehicles which may be co-transformed into a single cell, so that both individual chains are present and can form suitable disulfide bonds to form activated Factor VII. In certain embodiments of the present invention, surrounding conditions, such as pH, temperature and electrovalent charges in the medium can be adjusted to optimally promote proper disulfide bonding.

The modified FVII of the present invention can be administered by introducing nucleic acid (e.g., DNA, cDNA, RNA) encoding the modified FVII into the individual wherein the nucleic acid is expressed and FVIIa is expressed in vivo. Alternatively, the nucleic acid encoding the modified FVII can be administered ex vivo to cells (e.g., hepatocytes, myoblasts, fibroblasts, endothelial cells, keratinocytes, hematopoietic cells) of the individual and then transferred into the individual wherein the modified FVII is expressed and FVIIa is generated in vivo. For example, the nucleic acid (e.g., cDNA) encoding modified FVII can be cloned into an expression cassette that has a promoter (constitutive or regulatable) to drive transgene expression and a polyadenylation sequence downstream of the nucleic acid. Suitable promoters include the cytomegalovirus [CMV] promoter, and conditional promoters such as the dimerizer gene control system, based on the immunosuppressive agents FK506 and rapamycin, the ecdysone gene control system and the tetracycline gene control system. Also useful in the present invention may be the GeneSwitch™ technology [Valentis, Inc., Woodlands, Tex.] described in Abruzzese et al., Hum. Gene Ther. 1999 10:1499-507, the disclosure of which is hereby incorporated herein by reference.

In preferred embodiments, the DNA vectors used, whether they encode Factor VIIa, a modified Factor VII or separately the light chain of Factor VII and the heavy chain of Factor VII, may be introduced under the control of a regulatable promoter. The advantages of such a system are that the DNA vectors may be administered to the patient, and the serum levels of Factor VIIa may be closely monitored, as well as phenotypic parameters which indicate whether sufficient levels of blood coagulation are being achieved. With inducible or regulatable promoters, the clinician may exert additional optimization of the methods of the present invention, such that optimal levels of activated FVII are achieved for blood coagulation.

The expression cassette is then inserted into a vector such as adenovirus, partially-deleted adenovirus, fully-deleted adenovirus, adeno-associated virus (AAV), retrovirus, lentivirus, naked plasmid, plasmid/liposome complex, etc. for delivery to the host via intravenous, intramuscular, intraportal or other route of administration. Expression vectors which can be used in the methods and compositions of the present invention include, for example, viral vectors. One of the most frequently used methods of administration of gene therapy, both in vivo and ex vivo, is the use of viral vectors for delivery of the gene. Many species of virus are known, and many have been studied for gene therapy purposes. The most commonly used viral vectors include those derived from adenoviruses, adeno-associated viruses [AAV] and retroviruses, including lentiviruses, such as human immunodeficiency virus [HIV].

Adenoviral vectors for use to deliver transgenes to cells for applications such as in vivo gene therapy and in vitro study and/or production of the products of transgenes, commonly are derived from adenoviruses by deletion of the early region 1 (E1) genes (Berkner, K. L., *Curr. Top. Micro. Immunol.* 158L39-66 1992). Deletion of E1 genes renders such adenoviral vectors replication defective and significantly reduces expression of the remaining viral genes present within the vector. However, it is believed that the presence of the remaining viral genes in adenoviral vectors can be deleterious to the transfected cell for one or more of the following reasons: (1) stimulation of a cellular immune response directed against expressed viral proteins, (2) cytotoxicity of expressed viral proteins, and (3) replication of the vector genome leading to cell death.

One solution to this problem has been the creation of adenoviral vectors with deletions of various adenoviral gene sequences. In particular, pseudoadenoviral vectors (PAVs), also known as 'gutless adenovirus' or mini-adenoviral vectors, are adenoviral vectors derived from the genome of an adenovirus that contain minimal cis-acting nucleotide sequences required for the replication and packaging of the vector genome and which can contain one or more transgenes (See, U.S. Pat. No. 5,882,877 which covers pseudoadenoviral vectors (PAV) and methods for producing PAV, incorporated herein by reference). Such PAVs, which can accommodate up to about 36 kb of foreign nucleic acid, are advantageous because the carrying capacity of the vector is optimized, while the potential for host immune responses to the vector or the generation of replication-competent viruses is reduced. PAV vectors contain the 5' inverted terminal repeat (ITR) and the 3' ITR nucleotide sequences that contain the origin of replication, and the cis-acting nucleotide sequence required for packaging of the PAV genome, and can accommodate one or more transgenes with appropriate regulatory elements, e.g. promoter, enhancers, etc.

Other, partially deleted adenoviral vectors provide a partially-deleted adenoviral (termed "DeAd") vector in which the majority of adenoviral early genes required for virus replication are deleted from the vector and placed within a producer cell chromosome under the control of a conditional promoter. The deletable adenoviral genes that are placed in the producer cell may include E1A/E1B, E2, E4 (only ORF6 and ORF6/7 need be placed into the cell), pIX and pIVa2. E3 may also be deleted from the vector, but since it is not required for vector production, it can be omitted from the producer cell. The adenoviral late genes, normally under the control of the major late promoter (MLP), are present in the vector, but the MLP may be replaced by a conditional promoter.

Conditional promoters suitable for use in DeAd vectors and producer cell lines include those with the following characteristics: low basal expression in the uninduced state, such that cytotoxic or cytostatic adenovirus genes are not expressed at levels harmful to the cell; and high level expression in the induced state, such that sufficient amounts of viral proteins are produced to support vector replication and assembly. Preferred conditional promoters suitable for use in DeAd vectors and producer cell lines include the dimerizer gene control system, based on the immunosuppressive agents FK506 and rapamycin, the ecdysone gene control system and the tetracycline gene control system. Also useful in the present invention may be the GeneSwitch™ technology [Valentis, Inc., Woodlands, Tex.] described in Abruzzese et al., Hum. Gene Ther. 1999 10:1499-507, the disclosure of which is hereby incorporated herein by reference.

The partially deleted adenoviral expression system is further described in WO99/57296, the disclosure of which is hereby incorporated by reference herein.

Adenoviral vectors, such as PAVs and DeAd vectors, have been designed to take advantage of the desirable features of adenovirus which render it a suitable vehicle for delivery of nucleic acids to recipient cells. Adenovirus is a non-enveloped, nuclear DNA virus with a genome of about 36 kb, which has been well-characterized through studies in classical genetics and molecular biology (Hurwitz, M. S., Adenoviruses *Virology,* 3$^{rd}$ edition, Fields et al., eds., Raven Press, New York, 1996; Hitt, M. M. et al., Adenovirus Vectors, *The Development of Human Gene Therapy,* Friedman, T. ed., Cold Spring Harbor Laboratory Press, New York 1999). The viral genes are classified into early (designated E1-E4) and late (designated L1-L5) transcriptional units, referring to the generation of two temporal classes of viral proteins. The demarcation of these events is viral DNA replication. The human adenoviruses are divided into numerous serotypes (approximately 47, numbered accordingly and classified into 6 groups: A, B, C, D, E and F), based upon properties including hemaglutination of red blood cells, oncogenicity, DNA and protein amino acid compositions and homologies, and antigenic relationships.

Recombinant adenoviral vectors have several advantages for use as gene delivery vehicles, including tropism for both dividing and non-dividing cells, minimal pathogenic potential, ability to replicate to high titer for preparation of vector stocks, and the potential to carry large inserts (Berkner, K. L., *Curr. Top. Micro. Immunol.* 158:39-66, 1992; Jolly, D., *Cancer Gene Therapy* 1:51-64 1994).

PAVs have been designed to take advantage of the desirable features of adenovirus which render it a suitable vehicle for gene delivery. While adenoviral vectors can generally carry inserts of up to 8 kb in size by the deletion of regions which are dispensable for viral growth, maximal carrying capacity can be achieved with the use of adenoviral vectors containing deletions of most viral coding sequences, including PAVs. See U.S. Pat. No. 5,882,877 of Gregory et al.; Kochanek et al., *Proc. Natl. Acad. Sci. USA* 93:5731-5736, 1996; Parks et al., *Proc. Natl. Acad. Sci. USA* 93:13565-13570, 1996; Lieber et al., *J. Virol.* 70:8944-8960, 1996; Fisher et al., *Virology* 217: 11-22, 1996; U.S. Pat. No. 5,670,488; PCT Publication No. WO96/33280, published Oct. 24, 1996; PCT Publication No. WO96/40955, published Dec. 19, 1996; PCT Publication No. WO97/25446, published Jul. 19, 1997; PCT Publication No. WO95/29993, published Nov. 9, 1995; PCT Publication No. WO97/00326, published Jan. 3, 1997; Morral et al., *Hum. Gene Ther.* 10:2709-2716, 1998.

Since PAVs are deleted for most of the adenovirus genome, production of PAVs requires the furnishing of adenovirus proteins in trans which facilitate the replication and packaging of a PAV genome into viral vector particles. Most commonly, such proteins are provided by infecting a producer cell with a helper adenovirus containing the genes encoding such proteins.

However, such helper viruses are potential sources of contamination of a PAV stock during purification and can pose potential problems when administering the PAV to an individual if the contaminating helper adenovirus can replicate and be packaged into viral particles.

It is advantageous to increase the purity of a PAV stock by reducing or eliminating any production of helper vectors which can contaminate preparation. Several strategies to reduce the production of helper vectors in the preparation of a PAV stock are disclosed in U.S. Pat. No. 5,882,877, issued Mar. 16, 1999; U.S. Pat. No. 5,670,488, issued Sep. 23, 1997 and International Patent Application No. PCT/US99/03483, incorporated herein by reference. For example, the helper vector may contain mutations in the packaging sequence of its genome to prevent its packaging, an oversized adenoviral genome which cannot be packaged due to size constraints of the virion, or a packaging signal region with binding sequences that prevent access by packaging proteins to this signal which thereby prevents production of the helper virus.

Other strategies include the design of a helper virus with a packaging signal flanked by the excision target site of a recombinase, such as the Cre-Lox system (Parks et al., *Proc. Natl. Acad. Sci. USA* 93:13565-13570, 1996; Hardy et al., *J. Virol.* 71:1842-1849, 1997, incorporated herein by reference); or the phage C31 integrase [see Calos et al., WO 00/11555]. Such helper vectors reduce the yield of wild-type levels.

Another hurdle for PAV manufacturing, aside from the problems with obtaining helper vector-free stocks, is that the production process is initiated by DNA transfections of the PAV genome and the helper genome into a suitable cell line, e.g., 293 cells. After cytopathic effects are observed in the culture indicating a successful infection, which may take up to from 2 to 6 days, the culture is harvested and is passaged onto a new culture of cells. This process is repeated for several additional passages, up to 7 times more, to obtain a modes cell lysate containing the PAV vector and any contaminating helper vector. See Parks et al., 1996, *Proc. Natl. Acad. Sci. USA* 93:13565-13570; Kochanek et al., 1996, *Proc. Natl. Acad. Sci. USA* 93:5731-5736. This lengthy process is not optimal for commercial scale manufacturing. Additionally, this process facilitates recombination and rearrangement events resulting in the propagation of PAV genomes with unwanted alterations. The use of adenoviruses for gene therapy is described, for example, in U.S. Pat. No. 5,882,877; U.S. Patent, the disclosures of which are hereby incorporated herein by reference.

Adeno-associated virus (AAV) is a single-stranded human DNA parvovirus whose genome has a size of 4.6 kb. The AAV genome contains two major genes: the rep gene, which codes for the rep proteins (Rep 76, Rep 68, Rep 52, and Rep 40) and the cap gene, which codes for AAV replication, rescue, transcription and integration, while the cap proteins form the AAV viral particle. AAV derives its name from its dependence on an adenovirus or other helper virus (e.g., herpesvirus) to supply essential gene products that allow AAV to undergo a productive infection, i.e., reproduce itself in the host cell. In the absence of helper virus, AAV integrates as a provirus into the host cell's chromosome, until it is rescued by superinfection of the host cell with a helper virus, usually adenovirus (Muzyczka, *Curr. Top. Micor. Immunol.* 158:97-127, 1992).

Interest in AAV as a gene transfer vector results from several unique features of its biology. At both ends of the AAV genome is a nucleotide sequence known as an inverted terminal repeat (ITR), which contains the cis-acting nucleotide sequences required for virus replication, rescue, packaging and integration. The integration function of the ITR mediated by the rep protein in trans permits the AAV genome to integrate into a cellular chromosome after infection, in the absence of helper virus. This unique property of the virus has relevance to the use of AAV in gene transfer, as it allows for a integration of a recombinant AAV containing a gene of interest into the cellular genome. Therefore, stable genetic transformation, ideal for many of the goals of gene transfer, may be achieved by use of rAAV vectors. Furthermore, the site of integration for AAV is well-established and has been localized to chromosome 19 of humans (Kotin et al., *Proc. Natl. Acad. Sci.* 87:2211-2215, 1990). This predictability of integration site reduces the danger of random insertional events into the cellular genome that may activate or inactivate host genes or interrupt coding sequences, consequences that can limit the use of vectors whose integration of AAV, removal of this gene in the design of rAAV vectors may result in the altered integration patterns that have been observed with rAAV vectors (Ponnazhagan et al., *Hum Gene Ther.* 8:275-284, 1997).

There are other advantages to the use of AAV for gene transfer. The host range of AAV is broad. Moreover, unlike retroviruses, AAV can infect both quiescent and dividing cells. In addition, AAV has not been associated with human disease, obviating many of the concerns that have been raised with retrovirus-derived gene transfer vectors.

Standard approaches to the generation of recombinant rAAV vectors have required the coordination of a series of intracellular events: transfection of the host cell with an rAAV vector genome containing a transgene of interest flanked by the AAV ITR sequences, transfection of the host cell by a plasmid encoding the genes for the AAV rep and cap proteins which are required in trans, and infection of the transfected cell with a helper virus to supply the non-AAV helper functions required in trans (Muzyczka, N., *Curr. Top. Micor. Immunol.* 158:97-129, 1992). The adenoviral (or other helper virus) proteins activate transcription of the AAV rep gene, and the rep proteins then activate transcription of the AAV cap genes. The cap proteins then utilize the ITR sequences to package the rAAV genome into an rAAV viral particle. Therefore, the efficiency of packaging is determined, in part, by the availability of adequate amounts of the structural proteins, as well as the accessibility of any cis-acting packaging sequences required in the rAAV vector genome.

One of the potential limitations to high level rAAV production derives from limiting quantities of the AAV helper proteins required in trans for replication and packaging of the rAAV genome. Some approaches to increasing the levels of these proteins have included placing the AAV rep gene under the control of the HIV LTR promoter to increase rep protein levels (Flotte, F. R., et al., *Gene Therapy* 2:29-37, 1995); the use of other heterologous promoters to increase expression of the AAV helper proteins, specifically the cap proteins (Vincent, et al., *J. Virol.* 71:1897-1905, 1997); and the development of cell lines that specifically express the rep proteins (Yang, Q., et al., *J. Virol.,* 68:4847-4856, 1994).

Other approaches to improving the production of rAAV vectors include the use of helper virus induction of the AAV helper proteins (Clark, et al., *Gene Therapy* 3:1124-1132, 1996) and the generation of a cell line containing integrated copies of the rAAV vector and AAV helper genes so that infection by the helper virus initiates rAAV production (Clark et al., *Human Gene Therapy* 6:1329-1341, 1995).

rAAV vectors have been produced using replication-defective helper adenoviruses which contain the nucleotide sequences encoding the rAAV vector genome (U.S. Pat. No. 5,856,152 issued Jan. 5, 1999) or helper adenoviruses which contain the nucleotide sequences encoding the AAV helper proteins (PCT International Publication WO95/06743, published Mar. 9, 1995). Production strategies which combine high level expression of the AAV helper genes and the optimal choice of cis-acting nucleotide sequences in the rAAV vector genome have been described (PCT International Application No. WO97/09441 published Mar. 13, 1997).

Current approaches to reducing contamination of rAAV vector stocks by helper viruses, therefore, involve the use of temperature-sensitive helper viruses (Ensigner et al., *J. Virol.,* 10:328-339, 1972), which are inactivated at the non-permissive temperature. Alternatively, the non-AAV helper genes can be subcloned into DNA plasmids which are transfected into a cell during rAAV vector production (Salvetti et al., *Hum. Gene Ther.* 9:695-706, 1998; Grimm, et al., *Hum. Gene Ther.* 9:2745-2760, 1998; WO97/09441). The use of AAV for gene therapy is described, for example, in U.S. Pat. No. 5,753,500, the disclosures of each of the above are hereby incorporated herein by reference.

Retrovirus vectors are a common tool for gene delivery (Miller, *Nature* (1992) 357:455-460). The ability of retrovirus vectors to deliver an unrearranged, single copy gene into a broad range of rodent, primate and human somatic cells makes retroviral vectors well suited for transferring genes to a cell.

Retroviruses are RNA viruses wherein the viral genome is RNA. When a host cell is infected with a retrovirus, the genomic RNA is reverse transcribed into a DNA intermediate which is integrated very efficiently into the chromosomal DNA of infected cells. This integrated DNA intermediate is referred to as a provirus. Transcription of the provirus and assembly into infectious virus occurs in the presence of an appropriate helper virus or in a cell line containing appropriate sequences enabling encapsidation without coincident production of a contaminating helper virus. A helper virus is not required for the production of the recombinant retrovirus if the sequences for encapsidation are provided by co-transfection with appropriate vectors.

Another useful tool for producing recombinant retroviral vectors are packaging cell lines which supply in trans the proteins necessary for producing infectious virions, but those cells are incapable of packaging endogenous viral genomic nucleic acids (Watanabe & Termin, *Molec. Cell. Biol. (*1983) 3(12):2241-2249; Mann et al., *Cell* (1983) 33:153-159; Embretson & Temin, *J. Virol. (*1987) 61(9):2675-2683). One approach to minimize the likelihood of generating RCR in packaging cells is to divide the packaging functions into two genomes, for example, one which expresses the gag and pol gene products and the other which expresses the env gene product (Bosselman et al., *Molec. Cell. Biol. (*1987) 7(5): 1797-1806; Markowitz et al., *J. Virol.* (1988) 62(4):1120-1124; Danos & Mulligan, *Proc. Natl. Acad. Sci.* (1988) 85:6460-6464). That approach minimizes the ability for co-packaging and subsequent transfer of the two-genomes, as well as significantly decreasing the frequency of recombination due to the presence of three retroviral genomes in the packaging cell to produce RCR.

In the event recombinants arise, mutations (Danos & Mulligan, supra) or deletions (Boselman et al., supra; Markowitz et al., supra) can be configured within the undesired gene products to render any possible recombinants non-functional. In addition, deletion of the 3' LTR on both packaging constructs further reduces the ability to form functional recombinants.

The retroviral genome and the proviral DNA have three genes: the gag, the pol, and the env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication. Lentiviruses have additional genes including vit vpr, tat, rev, vpu, nef, and vpx (in HIV-1, HIV-2 and/or SIV). Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the result is a cis defect which prevents encapsidation of genomic RNA. However, the resulting mutant is still capable of directing the synthesis of all varion proteins.

Lentiviruses are complex retroviruses which, in addition to the common retroviral genes gag, poT and env, contain other genes with regulatory or structural function. The higher complexity enables the lentivirus to modulate the life cycle thereof, as in the course of latent infection. A typical lentivirus is the human immunodeficiency virus (HIV), the etiologic agent of AIDS. In vivo, HIV can infect terminally differentiated cells that rarely divide, such as lymphocytes and macrophages. In vitro, HIV can infect primary cultures of monocyte-derived macrophages (MDM) as well as HeLa-Cd4 or T lymphoid cells arrested in the cell cycle by treatment with aphidicolin or gamma irradiation. Infection of cells is dependent on the active nuclear import of HV preintegration complexes through the nuclear pores of the target cells. That occurs by the interaction of multiple, partly redundant, molecular determinants in the complex with the nuclear import machinery of the target cell. Identified determinants include a functional nuclear localization signal (NLS) in the gag matrix (MA) protein, the karyophilic virion-associated protein, vpr, and a C-terminal phosphotyrosine residue in the gag MA protein. The use of retroviruses for gene therapy is described, for example, in U.S. Pat. Nos. 6,013,516; and 5,994,136, the disclosures of which are hereby incorporated herein by reference.

Other methods for delivery of DNA to cells do not use viruses for delivery. For example, cationic amphiphilic compounds can be used to deliver the nucleic acid of the present invention. Because compounds designed to facilitate intracellular delivery of biologically active molecules must interact with both non-polar and polar environments (in or on, for example, the plasma membrane, tissue fluids, compartments within the cell, and the biologically active molecular itself), such compounds are designed typically to contain both polar and non-polar domains. Compounds having both such domains may be termed amphiphiles, and many lipids and synthetic lipids that have been disclosed for use in facilitating such intracellular delivery (whether for in vitro or in vivo application) meet this definition. One particularly important class of such amphiphiles is the cationic amphiphiles. In general, cationic amphiphiles have polar groups that are capable of being positively charged at or around physiological pH, and this property is understood in the art to be important in defining how the amphiphiles interact with the many types of biologically active (therapeutic) molecules including, for example, negatively charged polynucleotides such as DNA.

Examples of cationic amphiphilic compounds that have both polar and non-polar domains and that are stated to be useful in relation to intracellular delivery of biologically active molecules are found, for example, in the following references, which contain also useful discussion of (1) the properties of such compounds that are understood in the art as making them suitable for such applications, and (2) the nature of structures, as understood in the art, that are formed by complexing of such amphiphiles with therapeutic molecules intended for intracellular delivery.

(1) Felgner, et al., Proc. Natl. Acad. Sci. USA, 84, 7413-7417 (1987) disclose use of positively-charged synthetic cationic lipids including N->1(2,3-dioleyloxy)propyl!-N,N,N-trimethylammonium chloride ("DOTMA"), to form lipid/DNA complexes suitable for transfections. See also Felgner et al., The Journal of Biological Chemistry, 269(4), 2550-2561 (1994).

(2) Behr et al., Proc. Natl. Acad. Sci USA, 86, 6982-6986 (1989) disclose numerous amphiphiles including dioctadecylamidologlycylspermine ("DOGS").

(3) U.S. Pat. No. 5,283,185 to Epand et al. describes additional classes and species of amphiphiles including 3.beta.>N-(N.sup.1,N.sup.1-dimethylaminoethane) carbamoyl! cholesterol, termed "DC-chol".

(4) Additional compounds that facilitate transport of biologically active molecules into cells are disclosed in U.S. Pat. No. 5,264,618 to Felgner et al. See also Felgner et al., The Journal Of Biological Chemistry, 269(4), pp. 2550-2561 (1994) for disclosure therein of further compounds including "DMRIE" 1,2-dimyristyloxypropyl-3-dimethylhydroxyethyl ammonium bromide.

(5) Reference to amphiphiles suitable for intracellular delivery of biologically active molecules is also found in U.S. Pat. No. 5,334,761 to Gebeyehu et al., and in Felgner et al., Methods (Methods in Enzymology), 5, 67-75 (1993).

The use of compositions comprising cationic amphiphilic compounds for gene delivery is described, for example, in U.S. Pat. Nos. 5,049,386; 5,279,833; 5,650,096; 5,747,471;

5,767,099; 5,910,487; 5,719,131; 5,840,710; 5,783,565; 5,925,628; 5,912,239; 5,942,634; 5,948,925; 6,022,874; 5,994,317; 5,861,397; 5,952,916; 5,948,767; 5,939,401; and 5,935,936, the disclosures of which are hereby incorporated herein by reference.

In addition, nucleic acid encoding modified FVII of the present invention can be delivered using "naked DNA". Methods for delivering a non-infectious, non-integrating DNA sequence encoding a desired polypeptide or peptide operably linked to a promoter, free from association with transfection-facilitating proteins, viral particles, liposomal formulations, charged lipids and calcium phosphate precipitating agents are described in U.S. Pat. Nos. 5,580,859; 5,963,622; 5,910,488; the disclosures of which are hereby incorporated herein by reference.

Gene transfer systems that combine viral and nonviral components have also been reported. Cristiano et al., (1993) *Proc. Natl. Acad. Sci. USA* 90:11548; Wu et al. (1994) *J. Biol. Chem.* 269:11542; Wagner et al. (1992) *Proc. Natl. Acad. Sci. USA* 89:6099; Yoshimura et al. (1993) *J. Biol. Chem.* 268: 2300; Curiel et al. (1991) *Proc. Natl. Acad. Sci. USA* 88:8850; Kupfer et al. (1994) *Human Gene Ther.* 5:1437; and Gottschalk et al. (1994) *Gene Ther.* 1:185. In most cases, adenovirus has been incorporated into the gene delivery systems to take advantage of its endosomolytic properties. The reported combinations of viral and nonviral components generally involve either covalent attachment of the adenovirus to a gene delivery complex or co-internalization of unbound adenovirus with cationic lipid: DNA complexes.

As described herein, an effective amount of DNA vector encoding Factor VIIa, a modified FVII, or FVII light chain and FVII heavy chain is administered to the individual. An "effective amount" of DNA vectors encoding the FVIIa, modified FVII or the light and heavy chains of FVII, is an amount such that when administered, it produces biologically active FVII molecule, which results in enhanced blood clotting in the individual to whom it is administered relative to blood clotting when an effective amount of these vectors capable of producing activated FVII protein is not administered. In addition, the amount of modified FVII administered to an individual will vary depending on a variety of factors, including the size, age, body weight, general health, sex and diet of the individual, and the time of administration, duration or particular qualities of the blood clotting defect. In the particular embodiments wherein adenoviral or AAV vectors are used, the dose of the DNA encoding modified FVII can be delivered via adenoviral or AAV particles, generally in the range of about $10^6$ to about $10^{15}$ particles, more preferably in the range of about $10^8$ to about $10^{13}$ particles. In the particular embodiments wherein retroviral or lentiviral vectors are used, the dose of the DNA encoding modified FVII can be delivered via retroviral or lentiviral particles, generally in the range of about $10^4$ to about $10^{13}$ particles, more preferably in the range of about $10^6$ to about $10^{11}$ particles. When DNA is delivered in the form of plasmid DNA, a useful dose will generally range from about 1 ug to about 1 g of DNA, preferably in the range from about 100 ug to about 100 mg of DNA. The skilled clinician may also determine the suitable dosage based upon expression levels geared to meet particular plasma concentration levels of FVII. Normal plasma concentration levels are approximately 500 nanograms/ml. However, it is known that significant amounts of coagulation can be achieved with only a fraction of this concentration. Accordingly, the dosage of DNA encoding modified FVII to be used in the present invention may be tailored in order to achieve a FVII plasma concentration level of about 5 nanograms/ml to about 1000 nanograms/ml. Methods for measuring the plasma concentration levels of FVII are known in the art, and can be used to monitor and/or tailor the dosage regimen appropriately.

The DNA vector encoding modified FVII can be administered using a variety of routes of administration. For example, the modified FVII can be administered intravenously, parenterally, intramuscularly, subcutaneously, orally, nasally, by inhalation, by implant, by injection and/or by suppository. The composition can be administered in a single dose or in more that one dose over a period of time to confer the desired effect.

The present invention also provides compositions (e.g., pharmaceutical compositions) comprising the DNA vectors encoding the modified FVII described herein. In one embodiment, the Factor VII comprises an amino acid sequence which codes for a signal for precursor cleavage by furin at the activation cleavage site of the modified Factor VII. The compositions described herein can also include a pharmaceutically acceptable carrier. The terms "pharmaceutically acceptable carrier" or "carrier" refer to any generally acceptable excipient or drug delivery device that is relatively inert and non-toxic. Exemplary carriers include calcium carbonate, sucrose, dextrose, mannose, albumin, starch, cellulose, silica gel, polyethylene glycol (PEG), dried skim milk, rice flour, magnesium strearate and the like.

Other suitable carriers (e.g., pharmaceutical carriers) include, but are not limited to sterile water, salt solutions (such as Ringer's solution), alcohols, gelatin, carbohydrates such as lactose, amylose or starch, talc, silicic acid, viscous paraffin, fatty acid esters, hydroxymethylcellulose, polyvinyl pyrolidone, etc. Such preparations can be sterilized and, if desired, mixed with auxiliary agents, e.g., lubricants, preservatives, stabilizers, wetting agents, emulsifiers, salts for influencing osmotic pressure, buffers, coloring and/or aromatic substances and the like which do not deteriously react with the DNA vector encoding modified FVII. A carrier (e.g., a pharmaceutically acceptable carrier) is preferred, but not necessary to administer the DNA vector encoding modified FVII. Suitable formulations and additional carriers are described in Remington's Pharmaceutical Sciences ($17^{th}$ Ed., Mack Publ. Co., Easton, Pa.), the teachings of which are incorporated herein by reference in their entirety.

The present invention also relates to an expression vector comprising nucleic acid encoding a modified Factor VII, wherein the modified Factor VII leads to generation of Factor VIIa in vivo. In one embodiment, the nucleic acid sequence encodes an amino acid sequence which includes a signal for precursor cleavage by furin at the activation cleavage site of the modified Factor VII. In another embodiment, the nucleic acid construct comprises two expression constructs which encode a modified Factor VII wherein the first expression construct comprises amino acids 1-152 of human Factor VII and the second expression comprises amino acids 153-406 of human Factor VII and a leader sequence.

The present invention also relates to host cells comprising nucleic acid which encodes a modified Factor VII, wherein the modified Factor VII leads to generation of Factor VIIa in vivo. In one embodiment, the nucleic acid sequence encodes an amino acid sequence which includes a signal for precursor cleavage by furin at the activation cleavage site of the modified Factor VII. In another embodiment, the nucleic acid construct comprises two expression constructs which encode a modified Factor VII wherein the first expression construct comprises amino acids 1-152 of human Factor VII and the second expression comprises amino acids 153-406 of human Factor VII and a leader sequence.

EXAMPLES

Materials & Methods

Cloning of FVII:

The factor VII cDNA was cloned by PCR (Perkin Elmer, 25 cycles) from a human liver cDNA library (Clontech) using primer 5432JS (5'-CTAGCCTAGG CCACCATGGTCTC-CCAGGCC CTCAGGCTC-3') (SEQ ID NO. 12) and primer 5433JS (5'-CCTTAATTAA TAGGGAAAT GGGGCTCGCA GGAG-3') (SEQ ID NO. 13). The PCR product was cloned into a pCRBlunt-II TOPO vector (Invitrogen), sequenced for accuracy and then subcloned into pCMV expression vector, which has the CMV promoter/enhancer and an SV40 poly A.

Cloning of FVII Light Chain (LC):

The factor VII cDNA was cloned by PCR from the plasmid pCMV/hFVII using primer 5432JS shown above and primer 5479JS (5'-GCTAGCCTAT CGGCCTTGGG G-3') (SEQ ID NO. 14). This construct contains the FVII leader sequence and amino acids #1 (Ala) to #152 (Arg). The PCR product has been cloned into the pCR-Blunt-II TOPO vector, sequenced for accuracy and then subcloned into the pCMV expression vector.

Cloning of FVII Heavy Chain (HC):

The FVII heavy chain was cloned by three primer PCR from the plasmid pCMV/hFVII. The three primers used were 5432JS, 5433JS and primer 5480JS (5'-TGCACCGGCG CCGGCGCATT GTGGGGGGCA AGGTGT-3') (SEQ ID NO. 15). This construct contains the FVII leader sequence followed by amino acids #153 (Ile) to #406 (Pro). The PCR product has been cloned into pCR-Blunt-II TOPO vector, sequenced and then subcloned into the pCMV expression vector.

Mutagenesis to Create Furin Cleavage Site in FVII:

The cleavage site for the conversion of FVII to FVIIa has been mutated to a furin recognition site using three primer PCR mutagenesis method. The original amino acid sequence #149 (Pro) and #151 (Gly) has been changed to #149 (Arg) and #151 (Lys) to generate the furin recognition site $Arg^{149}$-Gln-Lys-$Arg^{152}$ (SEQ ID NO.10). The PCR product has been cloned into pCR-Blunt-II TOPO vector, sequenced and then subcloned into the pCMV expression vector.

In Vitro Transcription/Translation:

All clones mentioned above were tested by in vitro transcription/translation. The three clones were found to produce proteins of the expected sizes, that is, light chain=24 kd, heavy chain=34 kd and full length FVII=50 kd.

(6) Western Blot Analysis:

All plasmids were transfected into Hep3B cells (human hepatoma cell line) and FVII expression was measured at 24 hours by western blot analysis of the cell lysates using antibody to FVII obtained from Haematologic Technologies. All of the FVII clones expressed FVII proteins.

Membrane Contact Site Mutations:

It has been shown that certain mutations in the membrane contact site for factor VII can increase the membrane affinity of the protein (Shah et al (1998) PNAS, Vol. 95, 4229-4234) and increase the rate of autoactivation with soluble tissue factor compared to wild type factor VII. In one example of the present invention, we have combined these mutations (Pro-10 mutated to Gln and Lys-32 mutated to Glu) along with our mutations around amino acid 152 to generate a version of factor VII that are recognized by furin or SKI-1 and is more potent at FVII specific clotting. See FIG. 2.

(8) Generation of SKI-1 Recognition Sites for FVII Processing:

SKI-1 is a proprotein convertase that is present in the golgi of most tissues and cells and has a unique cleavage specificity (Seidah et al. (1999) PNAS, Vol. 96, 1321-1326). In one example of the present invention the cDNA for FVII is modified around amino acid 152 to create a recognition site for SKI-1, such that SKI-1 cleaves FVII to generate active FVIIa. See FIG. 3.

Cloning & Mutagenesis of Human FVII

Human FVII cDNA was PCR amplified from a human liver Quick Clone cDNA (Clontech) and cloned into pCMV, a plasmid containing the CMV promoter and SV40 polyA and pLSP, a plasmid containing the AAT promoter and BGH polyA. The endogenous FVII cleavage site was mutated to contain a furin recognition site using the primer 5' AGC AAA CGC CAA AAG CGA ATT GTG GGG GGC AAG 3') (SEQ ID NO. 16) which mutates Pro149 to an Arg and Gly151 to a Lys.

In Vitro Expression & Proteolytic Processing by Furin 293 and Hep3B cells were transfected with 10 ug pCMV/FVII or pCMV/FVIIa using either the Profection $CaPO_4$ Transfection Kit (Promega) or Lipofectamine 2000 (Gibco), respectively. In vitro expression of secreted FVIIa was detected using a FVIIa specific clotting assay described below.

To demonstrate proteolytic processing of FVII by furin, an in vitro transcription/translation reaction was done on the pCMV/FVII and pCMV/FVIIa plasmids. FVII was immunoprecipitated from the lysate using 2 ug of a polyclonal sheep anti-human FVII antibody (Haematologic Technologies) overnight at 4° C. A furin digest was done directly on the protein A sepharose beads in 100 mM Hepes, 0.5% Triton X-100, 1 mM CaCl2, 1 mM 2-mercaptoethanol and 2U of furin enzyme (NEB) at 30° C. for 1 hour. Following furin digestion, 20 uL of 2×SDS loading dye was added to the reaction and the entire sample was run on a 14% SDS PAGE gel.

Immunoprecipitation 293 cells were transfected with 10 ug pCMV/FVII and pCMV/FVIIa plasmids. 48 hours after transfection, cells were labeled with 35S-Met/Cys for 4 hours. FVII was immunoprecipitated from the cell lysate and media using 2 ug of a polyclonal sheep antihuman FVII antibody. Samples were run on a 14% SDS PAGE gel.

FVIIa Specific Clotting Assay

A FVIIa specific clotting assay, Staclot VIIa-rTF, was purchased from Diagnostica Stago. Clotting time was determined by adding 50 uL human FVII deficient plasma+50 uL rTF/pL+either 50 uL of supernatant from transfected cells or 50 uL of mouse plasma diluted 1:500 and incubating at 37° C. for 3 minutes. Clotting was initiated by adding 50 uL 0.025M $CaCl_2$ and the clotting time was measured on a Start 4 Clot Detection System (Diagnostica Stago).

Modified aPTT (Activated Partial Thromboplastin Time)

Figure 5:
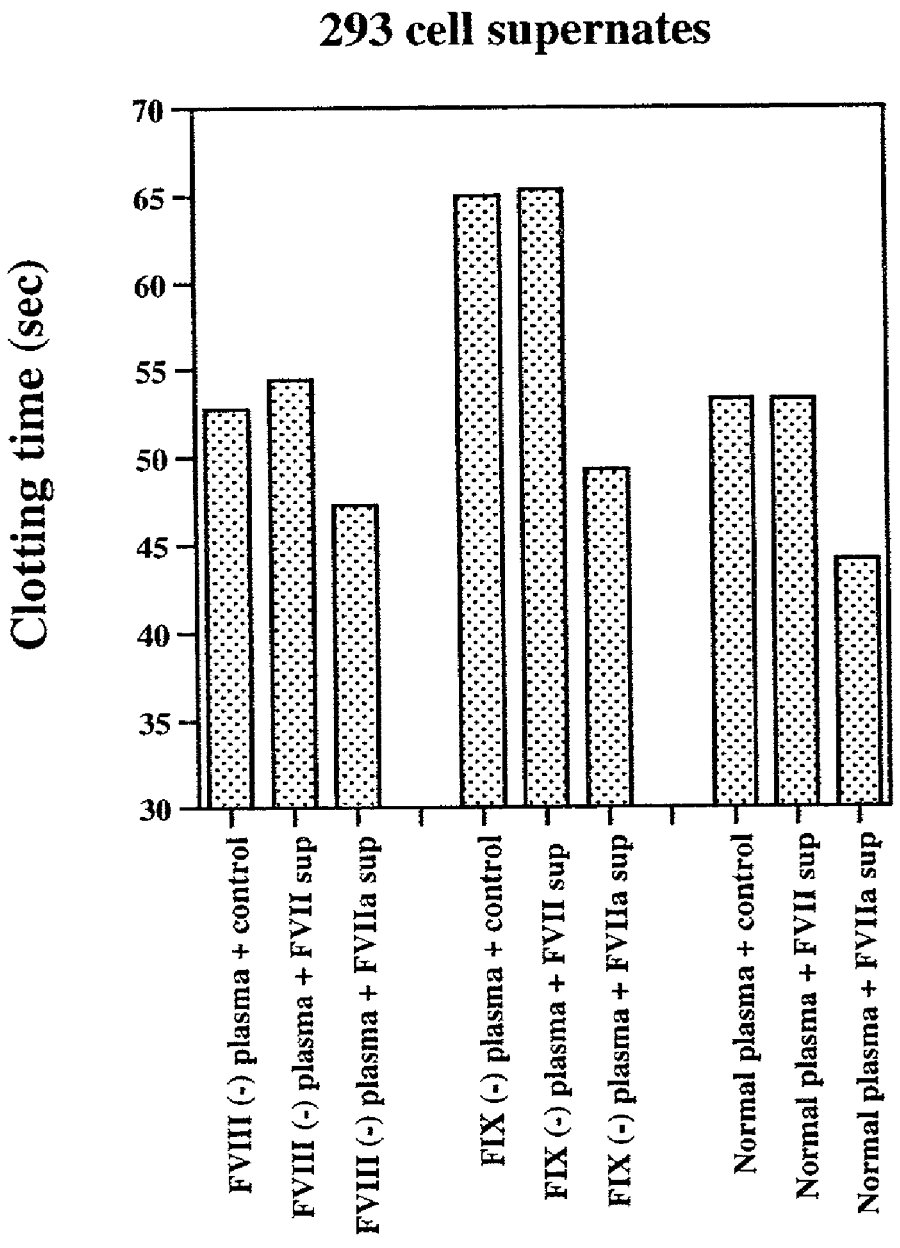
FIG. 5 illustrates clotting time in 293 cell supemates from normal, FVVIII-.

A modified APTT assay was performed by adding 50 uL of either human FVIII or FIX deficient plasma (George King Biomedical)+50 uL APTT reagent (Diagnostica Stago)+10 uL rTF/pL diluted 1:1000+50 uL of supernatant from Hep3B cells transfected with either pCMV/FVII or pCMV/FVIIa and incubating at 37° C. for 3 minutes. Clotting was initiated by adding 50 uL 0.025M $CaCl_2$ and the clotting time was measured on Start 4 Clot Detection System (Diagnostica Stago). See FIG. 5.

Diluted Partial Thromboplastin Time (PTT) Assay

Figure 6A:
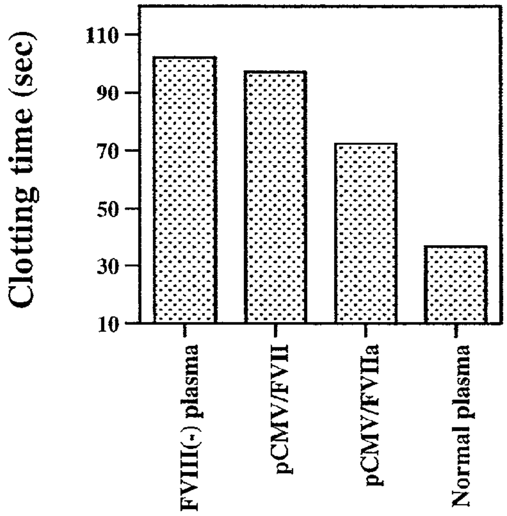
FIG. 6 illustrates clotting time in a modified aPTT assay.
Figure 6B:
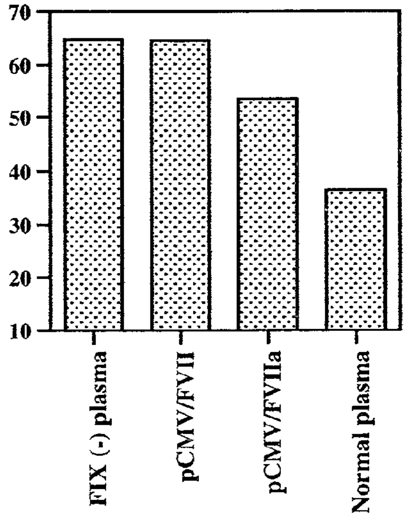

Diluted partial thromboplastin time was determined by incubating 50 uL of either human FVIII or FIX deficient plasma or normal human plasma+50 uL thromboplastin with calcium (Sigma) diluted 1:100 in 0.154M NaCl+50 uL media from 293 cells transfected with pCMV/FVII or pCMV/FVIIa and incubating at 37° C. for 3 minutes. Clotting was initiated by adding 50 uL 0.025M $CaCl_2$ and the clotting time was measured on Start 4 Clot Detection System (Diagnostica Stago). See FIG. 6.

In Vivo Studies in Normal & FVIII k/o Mice

Figure 7:
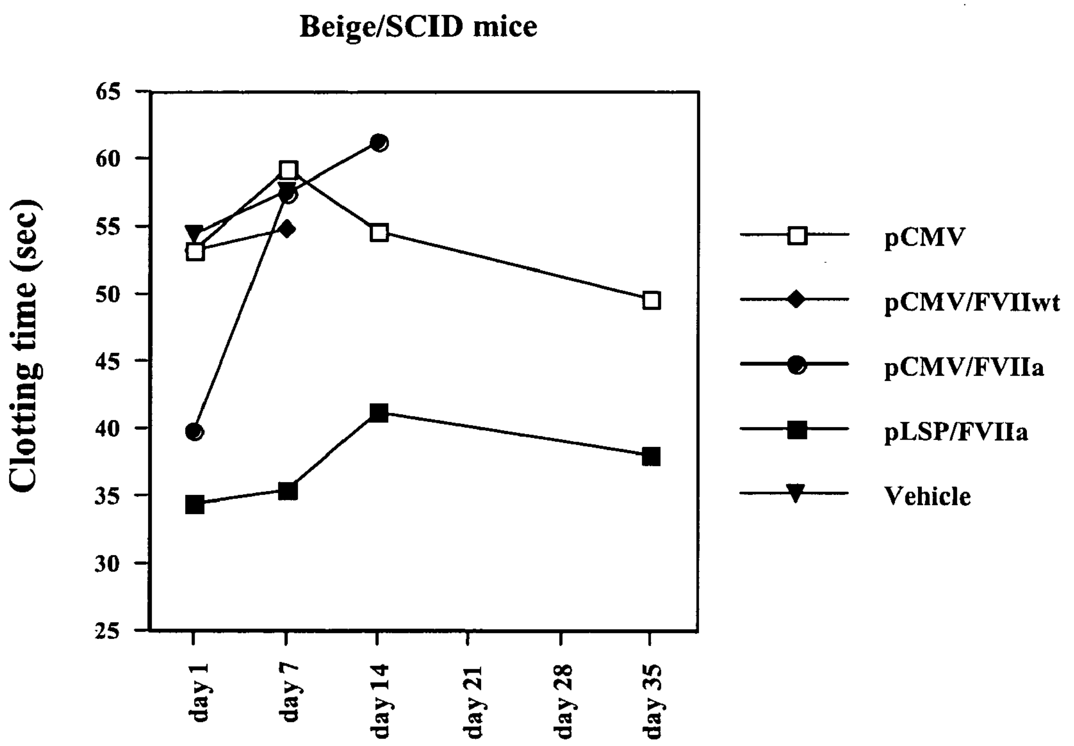
FIG. 7 illustrates clotting time in Beige/SCID mice transfected with FVII and FVIIa with CMV and liver-specific promoters [LSP].
Figure 8:
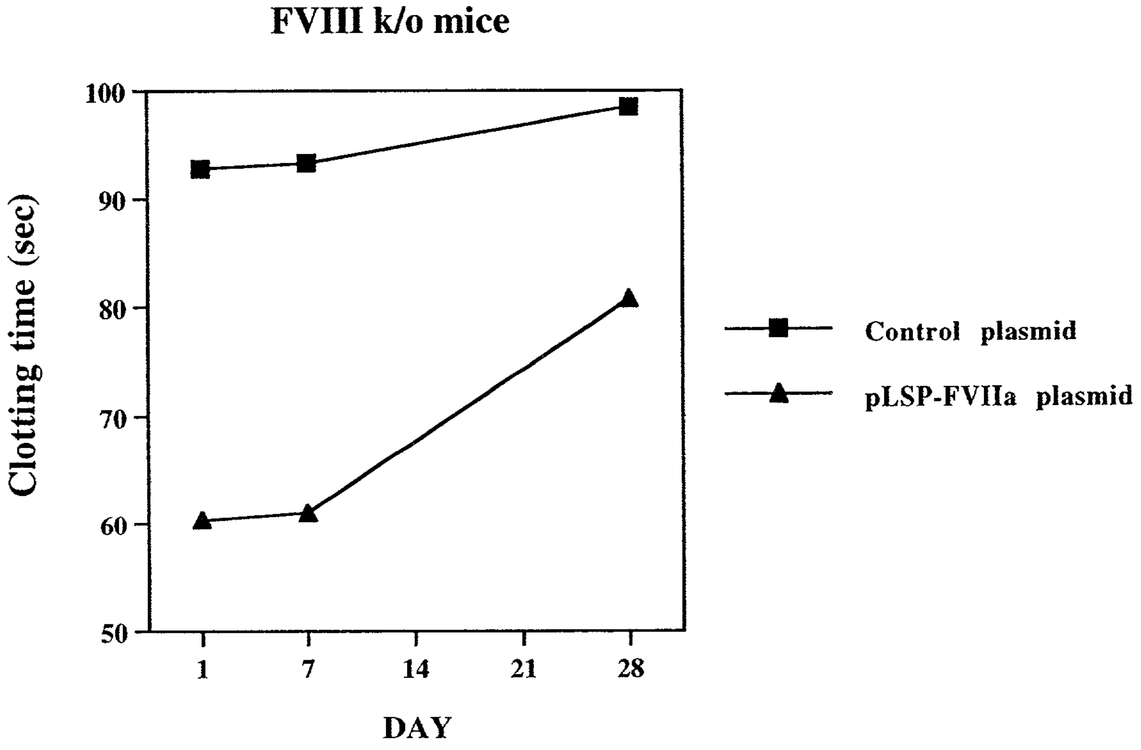
FIG. 8 illustrates clotting time in FVIII knockout mice transfected with FVIIa.
Figure 9:
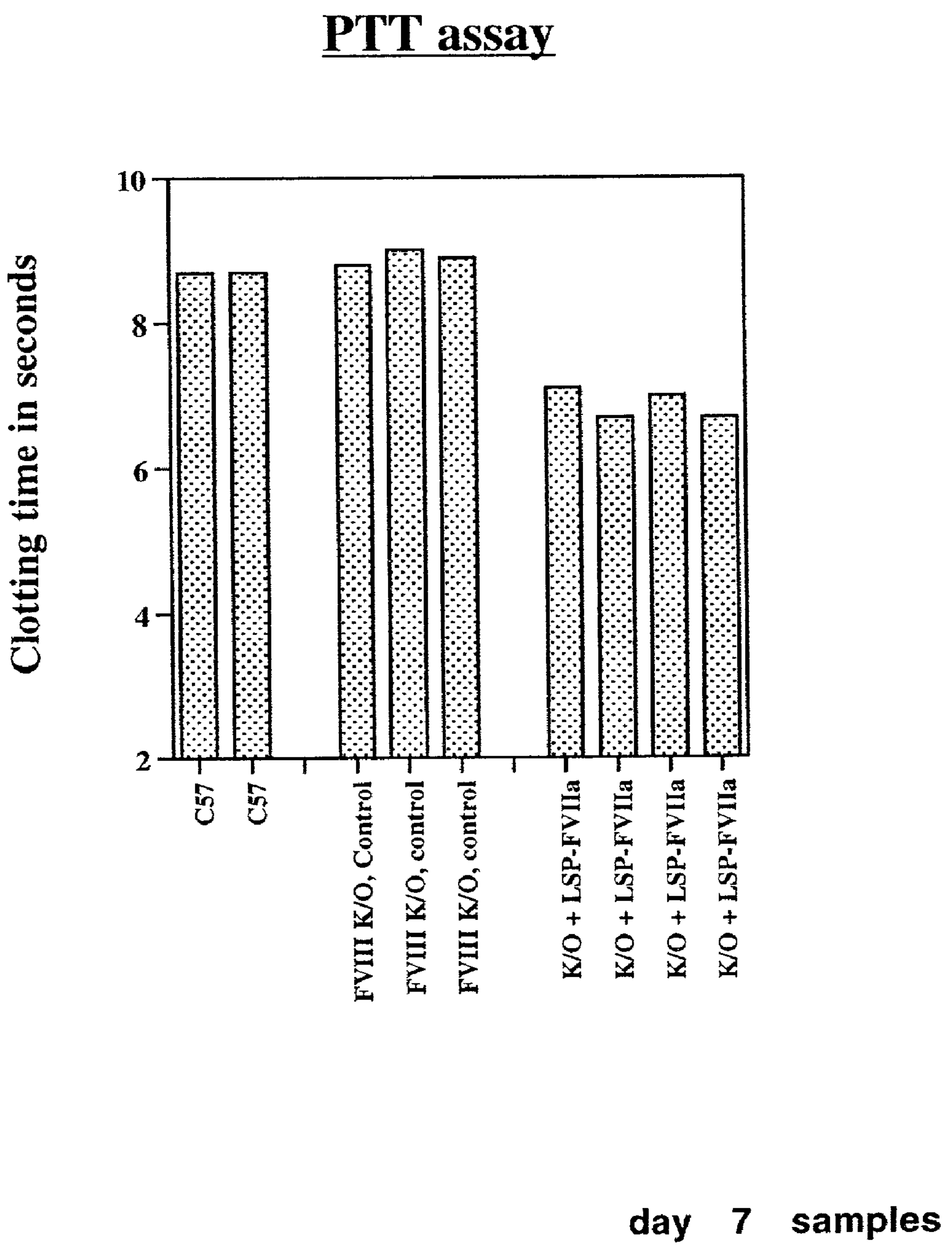
FIG. 9 illustrates clotting time in a PTT assay of FVIII knockout mice.

Beige/SCID and FVIII k/o mice were injected with 10 ug FVII or FVIIa plasmid via the tail vein using a high volume injection technique. Plasma was collected out to 5 weeks post injection. FVIIa was measured using the Staclot VIIa-rTF assay. See FIG. 7.

Prothrombin Time (PT) Assay

Prothrombin time was determined by incubating 50 uL of FVII KO mouse plasma at 37° C. for 1 minute. Clotting was initiated by adding 100 uL thromboplastin with calcium (Sigma Diagnostics) and the clotting time measured on Start 4 Clot Detection System (Diagnostica Stago).

While this invention has been particularly shown and described with references to preferred embodiments thereof, it will be understood by those skilled in the art that numerous modifications and changes in form and details and optimization of parameters may be made therein without departing from the scope of the invention encompassed by the appended claims. Such modifications, changes and optimizations constitute part of the present invention.

The disclosure of all of the publications which are cited in this specification are hereby incorporated herein by reference for the disclosure contained therein.

What is claimed is:

1. A method at promoting blood coagulation in an individual having a blood coagulation defect and in need thereof, comprising administering to the individual a blood coagulation enhancing effective amount of a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII and wherein at least one amino acid mutations have been made in said area to create said enzymatic cleavage site, and, whereby cleavage by furin produces two peptides comprising Factor VII heavy chain and Factor VII light chain molecules.

2. A method of promoting blood coagulation in an individual having a blood coagulation defect and in need thereof, comprising administering to the individual a blood coagulation enhancing effective amount of a DNA vector encoding a human Factor VII polypeptide that can be converted to Factor VIIa when expressed in said individual, said Factor VII polypeptide comprising an enzymatic cleavage site susceptible to cleavage by SKI-1, wherein said enzymatic cleavage site is located in the area of about amino acid 147 through about 154 of said Factor VII and wherein at least one amino acid mutations have been made in said area to create said enzymatic cleavage site, and, whereby cleavage by SKI-1 produces two peptides comprising Factor VII heavy chain and Factor VII light chain molecules.

3. A method according to claim 1, wherein said DNA vector further comprises a liver-specific promoter.

4. A method according to claim 2, wherein said DNA vector further comprises a liver-specific promoter.

5. A method of promoting blood coagulation in an individual having a blood coagulation defect and in need thereof, comprising administering to the individual a blood coagulation enhancing effective amount of a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site, and, whereby cleavage by furin produces Factor VII heavy chain and Factor VII light chain molecules, wherein amino acid 149 is changed from proline to arginine and amino acid 151 is changed from glycine to lysine.

6. A method of promoting blood coagulation in an individual having a blood coagulation defect and in need thereof, comprising administering to the individual a blood coagulation enhancing effective amount of a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site, and, whereby cleavage by furin produces Factor VII heavy chain and Factor VII light chain molecules, wherein amino acids 147 through 150 have been replaced by the amino acid sequence of SEQ ID NO. 17.

7. A method according to claim 5, wherein amino acids 147 through 154 have been replaced by the amino acid sequence of SEQ ID NO. 2.

8. A method according to claim 5, wherein amino acids 147 through 154 have been replaced by the amino acid sequence of SEQ ID NO. 5.

9. A method according to claim 5, wherein amino acids 147 through 154 have been replaced by the amino acid sequence of SEQ ID NO. 7.

10. A method of promoting blood coagulation in an individual having a blood coagulation defect and in need thereof, comprising administering to the individual a blood coagulation enhancing effective amount of a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site, and, whereby cleavage by furin produces Factor VII heavy chain and Factor VII light chain molecules, wherein amino acids 147 through 150 have been replaced by the amino acid sequence of SEQ ID NO. 18.

11. A method of promoting blood coagulation in an individual having a blood coagulation defect and in need thereof, comprising administering to the individual a blood coagulation enhancing effective amount of a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site, and, whereby cleavage by furin produces Factor VII heavy chain and Factor VII light chain molecules, wherein amino acids 148 through 151 have been replaced by the amino acid sequence of SEQ ID NO. 17.

12. A method of promoting blood coagulation in an individual having a blood coagulation defect and in need thereof, comprising administering to the individual a blood coagulation enhancing effective amount of a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site, and, whereby cleavage by furin produces Factor VII heavy chain and Factor VII light chain molecules, wherein amino acids 148 through 151 have been replaced by the amino acid sequence of SEQ ID NO. 18.

13. A method according to claim I of promoting blood coagulation in an individual having a blood coagulation defect and in need thereof, comprising administering to the individual a blood coagulation enhancing effective amount of a DNA vector encoding a human Factor VII polypeptide that can be converted to Factor VIIa when expressed in said individual, said Factor VII polypeptide composing an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site. and, whereby cleavage by furin Produces Factor VII heavy chain and Factor VII light chain molecules, wherein amino acids 150 through 153 have been replaced by the amino acid sequence of SEQ ID NO. 17.

14. A method of promoting blood coagulation in an individual having a blood coagulation defect and in need thereof, comprising administering to the individual a blood coagulation enhancing effective amount of a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site Is located in the area of about amino acid 147 through about 154 of said Factor VII, wherein at least one amino acid mutations have been made in said area to create said enzymatic cleavage site, and, whereby cleavage by furin produces Factor VII heavy chain and Factor VII light chain molecules, wherein amino acids 150 through 153 have been replaced by the amino acid sequence of SEQ ID NO. 18.

15. A method of promoting blood coagulation in an individual having a blood coagulation defect and in need thereof, comprising administering to the individual a blood coagulation enhancing effective amount of a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site, and, whereby cleavage by furin produces Factor VII heavy chain and Factor VII light chain molecules, wherein amino acids 151 through 154 have been replaced by the amino acid sequence of SEQ ID NO. 17.

16. A method of promoting blood coagulation in an individual having a blood coagulation defect and in need thereof, comprising administering to the individual a blood coagulation enhancing effective amount of a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site, and, whereby cleavage by furin produces Factor VII heavy chain and Factor VII light chain molecules, wherein amino acids 151 through 154 have been replaced by the amino acid sequence of SEQ ID NO. 18.

17. A method according to claims 1 or 2, wherein enhanced blood dotting results in the individual relative to blood clotting when an effective amount of the DNA vector is not administered.

18. A composition comprising a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site, and, whereby cleavage by furin produces two peptides comprising Factor VII heavy chain and Factor VII light chain molecules.

19. A composition comprising a DNA vector encoding a human Factor VII polypeptide that can be converted to Factor VIIa when expressed in said individual, said Factor VII polypeptide comprising an enzymatic cleavage site susceptible to cleavage by SKI-1, wherein said enzymatic cleavage site is located in the area of about amino acid 147 through about 154 of said Factor VII, wherein at least one amino acid mutations have been made in said area to create said enzymatic cleavage site, and whereby cleavage by SKI-1 produces two peptides comprising Factor VII heavy chain and Factor VII light chain molecules.

20. A composition according to claim 18, wherein said DNA vector further comprises a liver-specific promoter.

21. A composition according to claim 19, wherein said DNA vector further comprises a liver-specific promoter.

22. A composition comprising a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site and, wherein amino acid 149 is changed from proline to arginine and amino acid 151 is changed from glycine to lysine.

23. A composition comprising a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site and, wherein amino acids 147 through 150 have been replaced by the amino acid sequence of SEQ ID NO. 17.

24. A composition according to claim 22, wherein amino acids 147 through 154 have been replaced by the amino acid sequence of SEQ ID NO. 2.

25. A composition according to claim 22, wherein amino acids 147 through 154 have been replaced by the amino acid sequence of SEQ ID NO. 5.

26. A composition according to claim 22, wherein amino acids 147 through 154 have been replaced by the amino acid sequence of SEQ ID NO. 7.

27. A composition comprising a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site and, wherein amino acids 147 through 150 have been replaced by the amino acid sequence of SEQ ID NO. 18.

28. A composition comprising a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site and, wherein amino acids 148 through 151 have been replaced by the amino acid sequence of SEQ ID NO. 17.

29. A composition comprising a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site and, wherein amino acids 148 through 151 have been replaced by the amino acid sequence of SEQ ID NO. 18.

30. A composition comprising a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site and, wherein amino acids 150 through 153 have been replaced by the amino acid sequence of SEQ ID NO. 17.

31. A composition comprising a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site and, wherein amino acids 150 through 153 have been replaced by the amino acid sequence of SEQ ID NO. 18.

32. A composition comprising a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site and, wherein amino acids 151 through 154 have been replaced by the amino acid sequence of SEQ ID NO. 17.

33. A composition comprising a DNA vector encoding a human Factor VII polypeptide that can be converted to Factor VIIa when expressed in said individual, said Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site and, wherein amino acids 151 through 154 have been replaced by the amino acid sequence of SEQ ID NO. 18.

34. An expression vector comprising a nucleic acid sequence encoding a modified human Factor VII polypeptide comprising an enzymatic cleavage site susceptible to cleavage by furin, wherein said enzymatic cleavage site is located in the area of about amino acid 147 through about 154 of said Factor VII, wherein at least one amino acid mutations have been made in said area to create said enzymatic cleavage site, and whereby cleavage by furin produces two peptides comprising Factor VII heavy chain and Factor VII light chain molecules.

35. An expression vector comprising a nucleic acid sequence encoding a modified human Factor VII polypeptide comprising an enzymatic cleavage site susceptible to cleavage by SKI-1, wherein said enzymatic cleavage sits is located in the area of about amino acid 147 through about 154 of said Factor VII, wherein at least one amino acid mutations have been made in said area to create said enzymatic cleavage site, and whereby cleavage by SKI-1 produces two peptides comprising Factor VII heavy chain and Factor VII light chain molecules.

36. An expression vector comprising a nucleic acid sequence encoding a modified human Factor VII polypeptide comprising an enzymatic cleavage site susceptible to cleavage by furin, wherein said enzymatic cleavage site is located in the area of about amino acid 147 through about 154 of said Factor VII and wherein at least one amino acid mutations have been made in said area to create said enzymatic cleavage site, wherein amino acid 149 is changed from proline to arginine and amino acid 151 is changed from glycine to lysine.

37. An expression vector comprising a nucleic acid sequence encoding a modified human Factor VII polypeptide comprising an enzymatic cleavage site susceptible to cleavage by furin, wherein said enzymatic cleavage site is located in the area of about amino acid 147 through about 154 of said Factor VII and wherein at least one amino acid mutations have been made in said area to create said enzymatic cleavage site, wherein amino acids 147 through 150 have been replaced by the amino acid sequence of SEQ ID NO. 17.

38. An expression vector according to claim 36, wherein amino acids 147 through 154 have been replaced by the amino acid sequence of SEQ ID NO. 2.

39. An expression vector according to claim 36, wherein amino acids 147 through 154 have been replaced by the amino acid sequence of SEQ ID NO. 5.

40. An expression vector according to claim 36, wherein amino acids 147 through 154 have been replaced by the amino acid sequence of SEQ ID NO. 7.

41. An expression vector comprising a nucleic acid sequence encoding a modified human Factor VII polypeptide comprising an enzymatic cleavage site susceptible to cleavage by furin, wherein said enzymatic cleavage site is located in the area of about amino acid 147 through about 154 of said Factor VII and wherein at least one amino acid mutations have been made in said area to create said enzymatic cleavage site, wherein amino acids 147 through 150 have been replaced by the amino acid sequence of SEQ ID NO. 18.

42. An expression vector comprising a nucleic acid sequence encoding a modified human Factor VII polypeptide comprising an enzymatic cleavage site susceptible to cleavage by furin, wherein said enzymatic cleavage site is located in the area of about amino acid 147 through about 154 of said Factor VII and wherein at least one amino acid mutations have been made in said area to create said enzymatic cleavage site, wherein amino acids 148 through 151 have been replaced by the amino acid sequence of SEQ ID NO. 17.

43. An expression vector comprising a nucleic acid sequence encoding a modified human Factor VII polypeptide comprising an enzymatic cleavage site susceptible to cleavage by furin, wherein said enzymatic cleavage site is located in the area of about amino acid 147 through about 154 of said Factor VII and wherein at least one amino acid mutations have been made in said area to create said enzymatic cleavage site, wherein amino acids 14.8 through 151 have been replaced by the amino acid sequence of SEQ ID NO. 18.

44. An expression vector comprising a nucleic acid sequence encoding a modified human Factor VII polypeptide comprising an enzymatic cleavage site susceptible to cleavage by furin, wherein said enzymatic cleavage site is located in the area of about amino acid 147 through about 154 of said Factor VII and wherein at least one amino acid mutations have been made in said area to create said enzymatic cleavage site, wherein amino acids 150 through 153 have been replaced by the amino acid sequence of SEQ ID NO. 17.

45. An expression vector comprising a nucleic acid sequence encoding a modified human Factor VII polypeptide comprising an enzymatic cleavage site susceptible to cleavage by furin, wherein said enzymatic cleavage site is located in the area of about amino acid 147 throuoh about 154 of said Factor VII and wherein at least one amino acid mutations have been made in said area to create said enzymatic cleavage site, wherein amino acids 150 through 153 have been replaced by the amino acid sequence of SEQ ID NO. 18.

46. An expression vector comprising a nucleic acid sequence encoding a modified human Factor VII polypeptide comprising an enzymatic cleavage site susceptible to cleavage by furin, wherein said enzymatic cleavage site is located in the area of about amino acid 147 through about 154 of said Factor VII and wherein at least one amino acid mutations have been made in said area to create said enzymatic cleavage site, wherein amino acids 151 through 154 have been replaced by the amino acid sequence of SEQ ID NO. 17.

47. An expression vector comprising a nucleic acid sequence encoding a modified human Factor VII polypeptide comprising an enzymatic cleavage site susceptible to cleavage by furin, wherein said enzymatic cleavage site is located in the area of about amino acid 147 through about 154 of said Factor VII and wherein at least one amino acid mutations have been made in said area to create said enzymatic cleavage site, wherein amino acids 151 through 154 have been replaced by the amino acid sequence of SEQ ID NO. 18.

48. A composition according to claim 18, wherein said composition further comprises a pharmaceutically accepted carrier.

49. A composition according to claim 19, wherein said composition further comprises a pharmaceutically accepted carrier.

* * * * *

SEQUENCE LISTING

```
<160> NUMBER OF SEQ ID NOS: 20

<210> SEQ ID NO 1
<211> LENGTH: 8
<212> TYPE: PRT
<213> ORGANISM: Homo sapiens

<400> SEQUENCE: 1

Ser Lys Pro Gln Gly Arg Ile Val
1               5


<210> SEQ ID NO 2
<211> LENGTH: 8
<212> TYPE: PRT
<213> ORGANISM: Homo sapiens

<400> SEQUENCE: 2

Ser Lys Arg Gln Lys Arg Ile Val
1               5


<210> SEQ ID NO 3
<211> LENGTH: 13
<212> TYPE: PRT
<213> ORGANISM: Homo sapiens

<400> SEQUENCE: 3

Ser Lys Pro Gln Gly Arg Arg Arg Arg Ala Asn Ile Val
1               5                   10


<210> SEQ ID NO 4
<211> LENGTH: 12
<212> TYPE: PRT
<213> ORGANISM: Homo sapiens

<400> SEQUENCE: 4

Ser Lys Pro Gln Gly Arg Arg Arg Arg Ser Ile Val
1               5                   10


<210> SEQ ID NO 5
<211> LENGTH: 9
<212> TYPE: PRT
<213> ORGANISM: Homo sapiens
```

-continued

<400> SEQUENCE: 5

Ser Lys Arg Gln Lys Arg Ala Ile Val
1 5

<210> SEQ ID NO 6
<211> LENGTH: 11
<212> TYPE: PRT
<213> ORGANISM: Homo sapiens

<400> SEQUENCE: 6

Ser Lys Arg Gln Arg Arg Ala Asn Gly Gly Lys
1 5 10

<210> SEQ ID NO 7
<211> LENGTH: 8
<212> TYPE: PRT
<213> ORGANISM: Homo sapiens

<400> SEQUENCE: 7

Arg Lys Arg Gln Lys Arg Ile Val
1 5

<210> SEQ ID NO 8
<211> LENGTH: 4
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X = Any amino acid residue
<220> FEATURE:
<221> NAME/KEY: MISC_FEATURE
<222> LOCATION: (3)..(3)
<223> OTHER INFORMATION: X = Any amino acid residue

<400> SEQUENCE: 8

Arg Xaa Xaa Arg
1

<210> SEQ ID NO 9
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = Arg or Lys
<220> FEATURE:
<221> NAME/KEY: MISC_FEATURE
<222> LOCATION: (3)..(3)
<223> OTHER INFORMATION: X = Arg or Lys
<220> FEATURE:
<221> NAME/KEY: MISC_FEATURE
<222> LOCATION: (5)..(5)
<223> OTHER INFORMATION: X = Leu or Val or Phe

<400> SEQUENCE: 9

Xaa Lys Xaa Gln Xaa Arg Ile Val
1 5

<210> SEQ ID NO 10
<211> LENGTH: 4
<212> TYPE: PRT
<213> ORGANISM: Homo sapiens

<400> SEQUENCE: 10

Arg Gln Lys Arg
1

-continued

<210> SEQ ID NO 11
<211> LENGTH: 4
<212> TYPE: PRT
<213> ORGANISM: Homo sapiens

<400> SEQUENCE: 11

Pro Gln Gly Arg
1

<210> SEQ ID NO 12
<211> LENGTH: 39
<212> TYPE: DNA
<213> ORGANISM: Artificial
<220> FEATURE:
<223> OTHER INFORMATION: Oligonucleotide primer

<400> SEQUENCE: 12
ctagcctagg ccaccatggt ctcccaggcc ctcaggctc 39

<210> SEQ ID NO 13
<211> LENGTH: 34
<212> TYPE: DNA
<213> ORGANISM: Artificial
<220> FEATURE:
<223> OTHER INFORMATION: Oligonucleotide primer

<400> SEQUENCE: 13
ccttaattaa ctagggaaat ggggctcgca ggag 34

<210> SEQ ID NO 14
<211> LENGTH: 21
<212> TYPE: DNA
<213> ORGANISM: Artificial
<220> FEATURE:
<223> OTHER INFORMATION: Oligonucleotide primer

<400> SEQUENCE: 14
gctagcctat cggccttggg g 21

<210> SEQ ID NO 15
<211> LENGTH: 36
<212> TYPE: DNA
<213> ORGANISM: Artificial
<220> FEATURE:
<223> OTHER INFORMATION: Oligonucleotide primer

<400> SEQUENCE: 15
tgcaccggcg ccggcgcatt gtggggggca aggtgt 36

<210> SEQ ID NO 16
<211> LENGTH: 33
<212> TYPE: DNA
<213> ORGANISM: Artificial
<220> FEATURE:
<223> OTHER INFORMATION: Oligonucleotide primer

<400> SEQUENCE: 16
agcaaacgcc aaaagcgaat tgtggggggc aag 33

<210> SEQ ID NO 17
<211> LENGTH: 4
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X = Any amino acid residue -continued

<400> SEQUENCE: 17

Arg Xaa Lys Arg
1

<210> SEQ ID NO 18
<211> LENGTH: 4
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X = Any amino acid residue

<400> SEQUENCE: 18

Arg Xaa Arg Arg
1

<210> SEQ ID NO 19
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = Arg or Lys
<220> FEATURE:
<221> NAME/KEY: MISC_FEATURE
<222> LOCATION: (2)..(2)
<223> OTHER INFORMATION: X = Any amino acid residue
<220> FEATURE:
<221> NAME/KEY: MISC_FEATURE
<222> LOCATION: (4)..(4)
<223> OTHER INFORMATION: X = Any amino acid residue
<220> FEATURE:
<221> NAME/KEY: MISC_FEATURE
<222> LOCATION: (5)..(5)
<223> OTHER INFORMATION: X = Arg or Lys

<400> SEQUENCE: 19

Xaa Xaa Arg Xaa Xaa Arg
1               5

<210> SEQ ID NO 20
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = Arg or Lys
<220> FEATURE:
<221> NAME/KEY: MISC_FEATURE
<222> LOCATION: (2)..(2)
<223> OTHER INFORMATION: X = Any amino acid residue
<220> FEATURE:
<221> NAME/KEY: MISC_FEATURE
<222> LOCATION: (3)..(3)
<223> OTHER INFORMATION: X = Arg or Lys
<220> FEATURE:
<221> NAME/KEY: MISC_FEATURE
<222> LOCATION: (4)..(4)
<223> OTHER INFORMATION: X = Any amino acid residue
<220> FEATURE:
<221> NAME/KEY: MISC_FEATURE
<222> LOCATION: (5)..(5)
<223> OTHER INFORMATION: X = Leu or Val or Phe

<400> SEQUENCE: 20

Xaa Xaa Xaa Xaa Xaa Glx
1               5